US011896631B2

(12) United States Patent
Biffi et al.

(10) Patent No.: US 11,896,631 B2
(45) Date of Patent: Feb. 13, 2024

(54) PROBIOTICS FOR USE IN THE TREATMENT OF DIVERTICULOSIS AND DIVERTICULAR DISEASE

(71) Applicant: ALFASIGMA S.P.A., Bologna (IT)

(72) Inventors: Andrea Biffi, Urgnano (IT); Walter Fiore, Atrani (IT); Ruggero Rossi, Milan (IT)

(73) Assignee: ALFASIGMA S.P.A., Bologna (IT)

( * ) Notice: Subject to any disclaimer, the term of this patent is extended or adjusted under 35 U.S.C. 154(b) by 619 days.

(21) Appl. No.: 16/467,797

(22) PCT Filed: Dec. 15, 2017

(86) PCT No.: PCT/IB2017/057980
§ 371 (c)(1),
(2) Date: Jun. 7, 2019

(87) PCT Pub. No.: WO2018/109730
PCT Pub. Date: Jun. 21, 2018

(65) Prior Publication Data
US 2021/0236565 A1    Aug. 5, 2021

(30) Foreign Application Priority Data
Dec. 16, 2016 (IT) .......................... 102016000127498

(51) Int. Cl.
| | |
|---|---|
| *A01N 63/00* | (2020.01) |
| *A61K 35/747* | (2015.01) |
| *A23L 33/135* | (2016.01) |
| *A61K 9/00* | (2006.01) |
| *A61K 9/48* | (2006.01) |
| *A61K 35/745* | (2015.01) |
| *A61K 36/06* | (2006.01) |

(52) U.S. Cl.
CPC .......... *A61K 35/747* (2013.01); *A23L 33/135* (2016.08); *A61K 9/0031* (2013.01); *A61K 9/0056* (2013.01); *A61K 9/48* (2013.01); *A61K 35/745* (2013.01); *A61K 36/06* (2013.01)

(58) Field of Classification Search
CPC .................................................. A61K 35/747
See application file for complete search history.

(56) References Cited

U.S. PATENT DOCUMENTS

| | | | |
|---|---|---|---|
| 5,531,989 | A | 7/1996 | Paul |
| 5,716,615 | A | 2/1998 | Cavaliere Vesely et al. |
| 6,770,246 | B1 | 8/2004 | Husek |
| 7,510,734 | B2 | 3/2009 | Sullivan et al. |
| 11,400,124 | B2 | 8/2022 | Biffi |
| 11,464,814 | B2 | 10/2022 | Biffi |
| 11,591,416 | B2 | 2/2023 | Biffi et al. |
| 2002/0090416 | A1 | 7/2002 | Connolly |
| 2003/0031659 | A1 | 2/2003 | Farmer |
| 2003/0092163 | A1 | 5/2003 | Collins et al. |
| 2003/0157146 | A1 | 8/2003 | Rautonen et al. |
| 2003/0190369 | A1 | 10/2003 | Lovett |
| 2004/0170617 | A1 | 9/2004 | Finegold |
| 2005/0196480 | A1 | 9/2005 | Sullivan et al. |
| 2006/0057704 | A1 | 3/2006 | Schlothauer et al. |
| 2006/0067921 | A1 | 3/2006 | Conway |
| 2008/0081035 | A1 | 4/2008 | Parmely et al. |
| 2008/0193603 | A1 | 8/2008 | Hayes et al. |
| 2008/0241226 | A1 | 10/2008 | Abeln et al. |
| 2009/0061446 | A1 | 3/2009 | Niimi et al. |
| 2009/0098088 | A1 | 4/2009 | Taylor et al. |
| 2009/0220481 | A1 | 9/2009 | Maes et al. |
| 2009/0312282 | A1 | 12/2009 | Yoshida et al. |
| 2010/0074994 | A1 | 3/2010 | Harel et al. |
| 2010/0112564 | A1 | 5/2010 | Zhao et al. |
| 2011/0014167 | A1 | 1/2011 | Bindels et al. |
| 2011/0038837 | A1 | 2/2011 | Nishida et al. |
| 2011/0052538 | A1 | 3/2011 | Brown et al. |
| 2011/0166100 | A1 | 7/2011 | Wu |
| 2011/0305744 | A1 | 12/2011 | Russo |
| 2012/0251512 | A1 | 10/2012 | Farmer et al. |
| 2012/0269865 | A1 | 10/2012 | Roughead et al. |
| 2012/0301451 | A1 | 11/2012 | Braenning et al. |
| 2012/0322773 | A1 | 12/2012 | Pravda |
| 2016/0296569 | A1 | 10/2016 | Guglielmetti et al. |
| 2016/0348155 | A1 | 12/2016 | Guglielmetti et al. |
| 2017/0035816 | A1 | 2/2017 | Biffi |
| 2017/0202231 | A1 | 7/2017 | Budelli et al. |
| 2019/0192590 | A1 | 6/2019 | Biffi |
| 2019/0290706 | A1 | 9/2019 | Biffi et al. |
| 2019/0345268 | A1 | 11/2019 | Biffi et al. |
| 2021/0186075 | A1 | 6/2021 | Biffi et al. |
| 2022/0325234 | A1 | 10/2022 | Biffi et al. |

(Continued)

FOREIGN PATENT DOCUMENTS

| | | |
|---|---|---|
| CN | 1161795 A | 10/1997 |
| CN | 1701116 A | 11/2005 |

(Continued)

OTHER PUBLICATIONS

Mexican Office Action for MX Application No. MX/a/2016/002766 filed on Sep. 5, 2014 onbehalf of SOFAR S.P.A, dated Mar. 18, 2021 10 pages (English + Original).
Screenshot from the web-archive of the Milano University, Nov. 23, 2015, 2 pages (English + Original).
Allowanceof the Brazilian patent application BR 11 2016 005059 2published in the Official Bulletin No. 2651 of Oct. 26, 2021 (Portuguese Only).
Australian Examination Report for AU Application No. 2017367302 filed on Dec. 1, 2017 on behalf of SOFAR S.P.A, dated Jul. 23, 2021 4 pages.

(Continued)

*Primary Examiner* — Albert M Navarro
(74) *Attorney, Agent, or Firm* — Steinfl + Bruno LLP

(57) ABSTRACT

The present invention relates to the use of probiotics to control the inflammatory process of the colon in subjects with structural modifications of the colon wall, preferably in subjects with diverticulosis, and affected by diverticular disease.

20 Claims, 6 Drawing Sheets

(56) References Cited

U.S. PATENT DOCUMENTS

| | | |
|---|---|---|
| 2022/0339216 A1 | 10/2022 | Biffi et al. |
| 2022/0354910 A1 | 11/2022 | Biffi et al. |
| 2022/0370520 A1 | 11/2022 | Biffi et al. |
| 2022/0409676 A1 | 12/2022 | Biffi et al. |
| 2023/0052820 A1 | 2/2023 | Biffi |

FOREIGN PATENT DOCUMENTS

| | | |
|---|---|---|
| CN | 1840206 A | 10/2006 |
| CN | 101636173 A | 1/2010 |
| CN | 102919922 A | 2/2013 |
| CN | 103997899 A | 8/2014 |
| CN | 108743851 A | 11/2018 |
| CN | 109310719 A | 2/2019 |
| EP | 1145643 A1 | 10/2001 |
| EP | 2407532 A2 | 1/2012 |
| JP | H0517363 A | 1/1993 |
| JP | 2005508617 A | 4/2005 |
| JP | 2005534315 A | 11/2005 |
| JP | 2010512755 A | 4/2010 |
| JP | 2010161944 A | 7/2010 |
| JP | 2013515051 A | 5/2013 |
| RU | 2182008 C1 | 5/2002 |
| WO | 00/54788 A1 | 9/2000 |
| WO | 2003/090763 A1 | 11/2003 |
| WO | 2004/022727 A1 | 3/2004 |
| WO | 2005/001109 A2 | 1/2005 |
| WO | 2005/083122 A2 | 9/2005 |
| WO | 2006/050479 A2 | 5/2006 |
| WO | 2007/071815 A1 | 6/2007 |
| WO | 2007/140621 A1 | 12/2007 |
| WO | 2008/119012 A2 | 10/2008 |
| WO | 2008/148798 A2 | 12/2008 |
| WO | 2010/008272 A1 | 1/2010 |
| WO | 2010/008278 A1 | 1/2010 |
| WO | 2010/099824 A1 | 9/2010 |
| WO | 2011/036539 A1 | 3/2011 |
| WO | 2012/154738 A1 | 11/2012 |
| WO | 2014/068338 A1 | 5/2014 |
| WO | 2014/137211 A1 | 9/2014 |
| WO | 2015/000972 A1 | 1/2015 |
| WO | 2015/033304 A1 | 3/2015 |
| WO | 2015/033305 A1 | 3/2015 |
| WO | 2015/162570 A1 | 10/2015 |
| WO | 2015/172191 A1 | 11/2015 |
| WO | 2016/030320 A1 | 3/2016 |
| WO | 2017/195182 A1 | 11/2017 |
| WO | 2017/212433 A1 | 12/2017 |
| WO | 2018/100549 A1 | 6/2018 |
| WO | 2018/109520 A1 | 6/2018 |
| WO | 2018/109730 A1 | 6/2018 |
| WO | 2019/019961 A1 | 1/2019 |
| WO | 2019/053604 A1 | 3/2019 |
| WO | 2019/111189 A1 | 6/2019 |
| WO | 2021/053636 A1 | 3/2021 |
| WO | 2021/053639 A1 | 3/2021 |
| WO | 2021/053641 A2 | 3/2021 |
| WO | 2021/053642 A1 | 3/2021 |
| WO | 2021/090228 A1 | 5/2021 |
| WO | 2021/090228 A4 | 7/2021 |

OTHER PUBLICATIONS

Bacteriotherapy—Merriam-Webster Medical Dictionary, Archive Date: Apr. 26, 2016, 6 pages.
Bassi R. "Mesalazine + Lactobacillus paracasei CNCMI1572 vs Mesalazine alone in preventing recurrence of symptom of diverticular disease: a prospective, randomize, open-label study." *Colorectal Disease*, 2019 1 pages.
Bassi R. "Preventing recurrence of symptomatic diverticular disease of the colon: mesalazine with or without Lactobacillus case DG: a prospective randomized, open label study." European Society of Coloproctology, 2015, 1 page.
Canadian Office Action for CA Application No. 2,923,392 filed on Sep. 5, 2014 on behalf of SOFAR S.P.A, dated Apr. 1, 2021 4 pages.
Canani R. B. et al., "Potential beneficial effects of butyrate in intestinal and extraintestinal diseases" World Journal of Gastroenterology, vol. 17 No. 12, Mar. 2011, 10 pages.
Capsule (Pharmacy)—Wikipedia, the free encyclopedia, Archive Date: Apr. 10, 2016, 4 pages.
Chilean Office Action for CL Application No. 201901493 filed on Dec. 1, 2017 on behalf of SOFAR S.P.A, dated May 6, 2021 24 pages (English + Original).
Chinese Office Action for CN Application No. 201480049288X filed on Sep. 5, 2014 on behalf of SOFAR S.P.A, dated Aug. 12, 2021 (English + Original) 15 pages.
Chooi E. et al., "Chronic atrophic gastritis is a progressive disease: analysis of medical reports from Shanghai (1985-2009)" Singapore Med J, 2012, 53 (5), pp. 318-324.
Colledge H. "Atrophic Gastritis: Causes. Symptoms, & Treatment" *Healthline*, Sep. 2018, 5 pages.
Colombian Office Action for CO Application No. NC2018/0010950 filed on May 15, 2017 on behalf of SOFAR S.P.A, dated May 3, 2021 9 pages (English + Original).
Colombian Office Action for CO Application No. NC2018/0010954 filed on Jun. 2, 2019 on behalf of SOFAR S.P.A, dated Jun. 30, 2021 8 pages (Partial English + Original).
Colombian Office Action for CO Application No. NC2019/0007116 filed on Jul. 2, 2019 on behalf of SOFAR S.P.A, dated Sep. 29, 2021 12 pages (English + Original).
Colombian Office Action for Colombian Application No. NC2019/0006257 filed on Dec. 15, 2017 on behalf of SOFAR S.P.A, dated May 13, 2021 3 pages (English + Original).
Communication pursuant to Article 94(3) EPC for EP Application No. 17817173.2 filed on Dec. 1, 2017 on behalf of SOFAR S.P.A, dated Sep. 29, 2021 6 pages.
De Backer A. I. et al., "Intestinal stenosis from mesenteric injury after blunt abdominal trauma" Eur. Radiol., 1999, pp. 1429-1431.
Dore J. et al., "The Human Intestinal Microbiota; From Phylogenetics to Functional Metagenomics" *Old Herborn University*, 2010, pp. 15-26.
Dysbiosis—Wikipedia, the free encyclopedia, Dated: Mar. 31, 2014 https://web.archive.org/web/20140331225522/http://en.wikipedia.org/wiki/Dysbiosis , 4 pages.
Eurasian Office Action for EA Application No. 202090097/28 filed on Sep. 5, 2014 on behalf of SOFAR S.P.A, dated Aug. 16, 2021 (English + Original) 10 pages.
Ferrario, et al., "Modulation of Fecal Clostridiales Bacteria and Butyrate by Probiotic Intervention with Lactobacillus paracasei DG Varies among Healthy Adults1-3" J. Nutritional Epidemiology, 144. Sep. 3, 2014. pp. 1787-1796. 10 Pages.
Final Office Action for U.S. Appl. No. 14/916,961, filed Mar. 4, 2016, on behalf of SOFAR S.P.A, dated Oct. 14, 2021. 26 Pages.
Gould M. et al., "Diabetic diarrhea" Current Gastroenterology Report, 2009, pp. 354-359 (Abstract only).
Gould, M., et al., "Diabetic Diarrhea," Current Gastroenterology Reports, 11: 354-359. Full paper. 2009. 7 Pages.
Haenel H. "Human Normal and Abnormal Gastrointestinal Flora" *American Journal of Clinical Nutrition*, vol. 23 No. 11, Nov. 1970, pp. 1433-1439.
Iebba V. et al., "Eubiosis and Dysbiosis: the two sides of the microbiota" *New Microbiologica*, vol. 39, 2016, pp. 1-12.
Jarbrink-Sehgal M. E. et al., "Symptomatic Diverticulosis is Characterized by Loose Stools" *Clinical Gastroenterology and Hepatology*, 14: 1763-1770, Dec. 2016, 9 pages.
John Hopkins Medicine—Fecal Transplantation (Bacteriotherapy), John Hopkins Division of Gastroenterology and Hepatology, Archive Date: Apr. 2016, 2 pages.
Laval G. et al., "The use of steroids in the management of inoperable intestinal obstruction in terminal cancer patients: do they remove the obstruction?" Palliative Medicine, 2000, pp. 3-10.
Leonel, A.J., et al. "Butyrate: implications for intestinal function," Current Opinion in Clinical Nutrition and Metabolic Care 15(5): 474-479. 2012. 6 Pages.

(56) References Cited

OTHER PUBLICATIONS

Mangili G. et al., "Palliative care for intestinal obstruction in recurrent ovarian cancer: a multivariate analysis" *BMJ Journals*, 2005, 5 pages (Abstract Only).
Miceli E. et al., "Common Features of Patients with Autoimmune Atrophic Gastritis" *Clinical Gastroenterology and Hepatology*, 2012, pp. 812-814.
Non-Final Office Action for U.S. Appl. No. 16/465,237, filed May 30, 2019, on behalf of SOFAR S.P.A, dated Jul. 9, 2021. 37 Pages.
Notice of Allowance for U.S. Appl. No. 15/305,470, filed Oct. 20, 2016 on behalf of SOFAR S.P.A, dated Jun. 1, 2021 15 pages.
Notice of Allowance for U.S. Appl. No. 15/305,470, filed Oct. 20, 2016, on behalf of SOFAR SPA, dated Nov. 3, 2021. 8 Pages.
Notice of Allowance for U.S. Appl. No. 15/305,470, filed Oct. 20, 2016, on behalf of SOFAR SPA, dated Sep. 8, 2021. 8 Pages.
Notice of Allowance for U.S. Appl. No. 16/301,361, filed Nov. 13, 2018, on behalf of SOFAR S.P.A, dated Aug. 4, 2021. 11 Pages.
Restriction Requirement for U.S. Appl. No. 17/090,669, filed Nov. 5, 2020, on behalf of SOFAR S.P.A, dated Sep. 3, 2021. 7 Pages.
Rodriguez-Castro K. I. et al., "Clinical manifestations of chronic atrophic gastritis" Acta Biomed, vol. 89, 2018, pp. 88-92.
Salvetti E. et al., "The Genus *Lactobacillus*: A Taxonomic Update" *Probiotics & Antimicro. Prot.*, Nov. 2012, vol. 4, pp. 217-226.
Scarpignato C. et al., "Management of colonic diverticular disease in the third millennium: Highlights from a symposium held during the United European Gastroenterology Week 2017" Therapeutic Advances in Gastroenterology, vol. 11, Mar. 2018, pp. 1-21.
Tsimmerman Y. S. "Eubiosis and Dysbiosis of Gastrointestinal Tract: Myths and Reality" *Perm State Medical Academy*, 2013, 27 pages.
Wells D. "Gastritis Diet: What to Eat and What to Avoid" Healthline, Jul. 2020, 11 pages.
World Gastroenterology Organisation Global Guidelines "Probiotics and prebiotics" Feb. 2017, 35 pages.
Zhang, Z., et al., "Isolated exopolysaccharides from Lactobacillus rhamnosus GG alleviated adipogenesis mediated by TLR2 in mice," *Sci Rep* 6, 36083, Oct. 27, 2016. 13 Pages. https://doi.org/10.1038/srep36083.
Australian Examination Report for AU Application No. 2017263294 filed on May 15, 2017 on behalf of SOFAR S.P.A, dated Oct. 30, 2020 5 pages.
Chinese Decision of Rejection for CN Application No. 201480049296.4 filed on Sep. 5, 2014 on behalf of SOFAR S.P.A, dated Dec. 9, 2020 (English + Original) 12 pages.
Communication pursuant to Article 94(3) EPC for EP Application No. 14790322.3 filed on Sep. 5, 2014 on behalf of SOFAR S.P.A, dated Jan. 11, 2021 3 pages.
Cui Y. et al., "Revolution of Chronic Diarrhoea" China Medicine, Science, and Technology Publishing House, 1st edition, Jan. 2013, pp. 19-23 (Original + Partial Google Translation).
Israeli Office Action for IL Application No. 244391 filed on behalf of SOFAR S.P.A, dated Oct. 27, 2020 (English + Original) 4 pages.
Kay, RM., et al., "Dietary Fiber," J. of Lipid Research, v. 23, 1982. 221-242, 22 Pages.
Non-Final Office Action for U.S. Appl. No. 14/916,961, filed Mar. 4, 2016, on behalf of SOFAR S.P.A, dated Jan. 7, 2021. 22 Pages.
Restriction Requirement for U.S. Appl. No. 16/465,237, filed May 30, 2019 on behalf of SOFAR S.P.A, dated Dec. 21, 2020 8 pages.
Wang Y. et al., "Emerging Infectious Diseases" Science and Technology Documents Publishing House, 1st edition, Jan. 2006, pp. 310-312 (Original + Partial Google Translation).
Watanabe I. et al., "KT-11" *Food Style 21*, vol. 17, No. 6, pp. 62-64,2013. 5 pages (Machine Translation + Original).
Di Mario et al., "Use of Mesalazine in Diverticular Disease," J Clin Gastroenterol 40: S155-S159 (2006).
Tursi et al., "Mesalazine and/or Lactobacillus casei in Preventing Recurrence of Symptomatic Uncomplicated Diverticular Disease of the Colon: A Prospective, Randomized, Open-label Study," J Clin Gastroenterol 40: 312-316 (2006).

Tursi et al., "Balsalazide and/or high-potency probiotic mixture (VSL#3) in maintaining remission after attack of acute, uncomplicated diverticulitis of the colon," Int J Colorectal Dis 22: 1103-1108 (2007).
Tursi et al., "Randomised clinical trial: mesalazine and/or probiotics in maintaining remission of symptomatic uncomplicated diverticular diesase—a double-blind, randomised, placebo-controlled study," Aliment Pharmacol Ther 38: 741-751 (2013).
Ausubel et al, Current Protocols in molecular biology, edited vols. 1 and 2. John Wiley & Sons, Inc., Media, PA,1994.
Balzaretti et al., "A Novel rhamnose-rich heterp-exopolysaccharide isolated from Lactobacillus paracasei DG activates THP-1 human monocytic cells" *University of Huddersfiled Repository Article for Applied and Environmental Microbiology*.Jan. 17, 2017.
Balzaretti et al., "Exploring Lactobacillus paracasei probiosis and metabolic potential", University of Milan PhD thesis, 2015, pp. 1-132.
Ciucanu I. et al. "A simple and rapid method for the permethylation of carbohydrates" *Carbohydrate Research*,131(1984) pp. 209-217.
Collins M.N. and Birkinshaw C. "Hyaluronic acid based scaffolds for tissue engineering—A review", Carbohydrate Polymers 2013, 1262-1279.
Communication pursuant to Article 94(3) EPC for EP Application No. 14790322.3 filed on Sep. 5, 2014 on behalf of SOFAR S.P.A, dated Jan. 31, 2020 8 pages.
De Souza M.M. et aJ. "Effects of budesonide and probiotics enemas on the systemic inflammatory response of rats with experimental coJitis", Acta Cirurgica Brasileira 2007, 22 (Supp 1. 1 ): 40-45.
D'Inca R. et al. Rectal administration of Lactobacillus Casei DG modifies flora composition and Toll-Like receptor expression in colonic mucosa of patients with mildulcerative colitis\ Dig. Dis. Sci. 2011, 56: 1178-1187.
EFSA Journal, "Scientific Opinion on the maintenance of the list of QPS biological agents intentionally added to food and feed (2012 update)1" EFSA Journal2012; 10(12):3020. 84 pages.
European Food Safety Authority EFSA journal (2012) 10(6): 2723.
Evans S. "Clinical trial structures" *J Exp Stroke Transl Med*.Mar. 2011, pp. 1-16, 16 pages.
"Example Cross-Over Study Design {A Phase 11, Randomized, Double-Blind Crossover Study of Hypertena and Placebo in Participants with High Blookd Pressure)". ClinicalTrials.gov (2012).
Fakhari A. and Berkland C. "Applications and emerging trends of hyaluronic acid in tissue engineering, as a dermal filler and in osteoarthritis treatment", Acta Biomaterialia2013, 9, 7081-7092.
Fao and Who et al; "Live microorganisms which, when administered in adequate amounts, confer a health benefit on the host", *World Health Organizations and Food Agriculture Organization*. 2001.
Farup et al., "Probiotics, Symptoms, and Gut Microbiota; What are the relations? A Randomized Controlled Trial in Subjects with Irritable Bowel Syndrome" Gastro Research and Practice, vol. 2012. 7 pages.
Ferrario et al J. Nutrition (published online Sep. 3, 2014) 144: 1787-1796 (Year: 2014).
Final Office Action for U.S. Appl. No. 14/916,959, filed Mar. 4, 2016 on behalf of SOFAR SPA, dated Jul. 23, 2019. 23 pages.
Final Office Action for U.S. Appl. No. 14/916,961, filed Mar. 4, 2016 on behalf of SOFAR S.P.A dated Jan. 2, 2020 16 pages.
Final Office Action for U.S. Appl. No. 14/916,961, filed Mar. 4, 2016 on behalf of SOFAR S.P.A, dated Mar. 13, 2018. 15 pages.
Final Office Action for U.S. Appl. No. 15/305,470, filed Oct. 20, 2016 on behalf of SOFAR SPA, dated Jan. 14, 2019. 10 pages.
Final Office Action for U.S. Appl. No. 14/916,959, filed Mar. 4, 2016 on behalf of SOFAR SPA, dated Apr. 20, 2018. 26 pages.
Floch M.H. et al. "Recommendations for probiotic use—2011 Update", J. Clin.Gastroenterol.2011, 45: S168-S171.
Food and Agriculture Organization. Health and nutritional properties of probiotics in food including powder milk with live lactic acid bacteria.Oct. 2001 : 34 pages.
Gerwig G. et al., "Determination of the absolute configuration of mono-saccharides in complex carbohydrates by capillary G.L.C." *Carbohydrate Research*,77(1979) pp. 1-7.

(56) References Cited

OTHER PUBLICATIONS

Gill et al., "Metagenomic Analysis of the Human Distal Gut Microbiome," Science 312: 1355-1359 (2006).
Guglielmetti S. et al., "TgaA, a VirB1-Like Component Belonging to a Putative Type IV Secretion System of Bifidobacterium bifidum MIMBb75" *Applied and Environmental Microbiology*,vol. 80, No. 17,Sep. 2014 pp. 5161-5169.
Gugliemetti et al., "Randomised clinical trial; Bifidobacterium bifidum MIMBb75 significatnly alleviates irritable bowel syndrome and improves quality of life, a double-blind, placebo-controlled study" Alimentary Pharmacology & Therapeutics, p. 1123-1132. 2011.
Havea P. "Protein interactions in milk protein concentrate powders" *International Dairy Journal*,vol. 16,2006, pp. 415-422.
International Search Report for International Application No. PCT/IB2014/064284 filed on Sep. 5, 2014 on behalf of SOFAR SPA, dated Jan. 26, 2015. 6 pages.
International Search Report for International Application No. PCT/IB2014/064285 filed on Sep. 5, 2014 on behalf of SOFAR SPA, dated Jan. 29, 2015. 4 pages.
International Search Report for International Application No. PCT/IB2017/052850 filed on May 15, 2017 on behalf of SOFAR SPA, dated Aug. 17, 2017. 4 pages.
International Search Report for International Application No. PCT/IB2017/053389 filed on Jun. 8, 2017 on behalf of SOFAR SPA, dated Oct. 6, 2017. 5 pages . . . .
International Search Report for International Application No. PCT/IB2017/057576 filed on Dec. 1, 2017 on behalf of SOFAR SPA, dated Feb. 22, 2018. 5 pages.
International Search Report for International Application No. PCT/IB2017/057980 filed on Dec. 15, 2017 on behalf of SOFAR SPA, dated Mar. 19, 2018. 4 pages.
International Search report for International Application PCT/IB2015/052938 filed on Apr. 22, 2015 on behalf of SOFAR SPA, dated Jul. 31, 2015. 4 pages.
Italia il Ministero della Salute (*Linee Guida su Probiotici e Prebiotici rev*.May 2013).
Jacobsen et al., "Screening of Probiotic Activities of Forty-Seven Strains of Lactobacillus spp. by In Vitro techniques and Evaluation of the Colonization Ability of Five Selected Strains in Humans" Applied and Environmental Microbiology, Nov. 1999, p. 4949-4956. 8 pages.
Larsen et al., "Predominant genera of fecal microbiota in children with atopic dermatitis are not altered by intake of probiolic bacteria Lactobacillus acidophilus NCFM and *Bifidobacterium animalis* subsp. *lacis* Bi-07," FEMS Microbiol Ecol 75: 482-496 (2011).
Laws et al., "Biosynthesis, characterization, and design of bacterial exopolysacharides from lactic acid bacteria", *Biotechnology Advances*. vol. 19,2001. pp. 597-625.
LeBlanc et al., "Beneficial effects on host energy metabolism of shot-chain fatty acids and vitamins produced by commensal and probiotic bacteria," Microbial Cell Factories 16:79: 1-10 (2017).
Lombardo L; et al "New insights into Lactobacillus and functional intestinal disorders", Minerva Gastroenterologica E Dietologica, Edizioni Minerva Medica, Torino, IT, vol. 54, No. 3. 2008.
Lombardo, Lucio et al., "Clinical Evaluation of *Lactobacillus paracasei* Subsp. *paracasei* F19 with Gluco-Oligosaccharides in the Short-term Treatment of Irritable Bowel Syndrome" Microbial Ecology in Health and Disease 21: 28-32 (2009).
Martin R. et al. "Role of commensal and probiotic bacteria in human health: a focus on inflammatory bowel disease", Microbial Cell Factories2013, 12: 71.
Matthes H. et al. "Clinical trial: probiotic treatment of acute distal ulcerative colitis with rectally administered *Escherichia coli* Nissle I 917 (EcN)", BMC Complementaty and Alternative Medicine2010, 10: 13.
Mazzuoli S. et al. "Definition and evaluation of mucosal healing in clinical practice", Digestive and Liver Disease2013, 45, 969-977.

Michail et al., "Gut Microbiota is Not Modified by Randmized, Double-Blind, Placebo-Controlled Trial of VSL #3 in Diarrhea-Predominant Irritable Bowel Syndrome". (Probiotics & Antimicro Prot. (2011) 3: 1-7).
Milani et al., Assessing the fecal microbiota: and optimized ion torrent 16S rRNA gene-based analysis protocol. PLoS One. 2013; 8(7); e68739, 12 pages. Published2013 . . . .
Montalto M. et al., "Clinical trial: the effects of a probiotic mixture on non-steroidal anti-inflammatory drug enteropathy—a randomized, double-blind, cross-over, placebo-controlled study" *Aliment Pharmacol Ther*,2010, pp. 209-214, 6 pages.
Muyzer et al., "Profiling of Complex Microbial Populations by Denaturing Gradient Gel Electrophoresis Analysis of Polymerase Chain Reaction-Amplified Genes Coding for 16S rRNA," Applied and Environmental Microbiology 59:595-700(1993).
Necas J. et al. "Hyaluronic acid (hyaluronan): a review", Veterinarni Medicina, 2008, 53(8): 397-411.
Neiwert et al., "Structural Investigation of rhamnose-rich polysaccharides from *Streptococcus dysgalactiae* bovine mastitis isolate" Carbohydrate Research, vol. 389,2014. pp. 192-195.
Non-Final Office Action for U.S. Appl. No. 14/916,961, filed Mar. 4, 2016 on behalf of SOFAR S.P.A, dated Jun. 30, 2017. 21 pages.
Non-Final Office Action for U.S. Appl. No. 14/916,961, filed Mar. 4, 2016 on behalf of SOFAR S.P.A, dated Jul. 25, 2019. 18 pages . . . .
Non-Final Office Action for U.S. Appl. No. 15/305,470, filed Oct. 20, 2016 on behalf of SOFAR SPA, dated Aug. 22, 2019. 8 pages.
Non-Final Office Action for U.S. Appl. No. 16/301,361, filed Nov. 13, 2018 on behalf of SOFAR S.P.A, dated May 8, 2020 20 pages.
Non-Final Office Action for U.S. Appl. No. 14/916,959, filed Mar. 4, 2016 on behalf of SOFAR S.P.A, dated Mar. 13, 2020 25 pages.
Non-Final Office Action for U.S. Appl. No. 14/916,959, filed Mar. 4, 2016 on behalf of SOFAR SPA, dated Aug. 31, 2017. 27 pages.
Non-Final Office Action for U.S. Appl. No. 14/916,959, filed Mar. 4, 2016 on behalf of SOFAR SPA, dated Nov. 19, 2018. 15 pages.
Non-Final Office Action for U.S. Appl. No. 15/305,470, filed Oct. 20, 2016 on behalf of SOFAR SPA, dated Mar. 26, 2018. 10 pages.
Office Action in corresponding Chinese Patent Application No. 201480049296.4, dated Aug. 27, 2019.
Office Action in Corresponding Japanese Patent Application No. 2016-564193, dated Apr. 2, 2019.
Okuda et al., "Virtual metagenome reconstruction from 16S rRNA gene sequences".*Nature Communications*,2012. 8 pages.
Oliva S. et al. "Randomised clinical trial: the effectiveness of Lactobacillus Reuteri ATCC 55730 rectal enema in children with active distal ulcerative colitis", Aliment. Pharmacol. Ther.2012, 35: 327-334.
Olveira et al; "Lactobacillus paracasei Reduces Intestinal Inflammation in Adoptive Transfer Mouse Model of Experimental Colitis", Clinical and Developmenta Immunology, vol. 23, No. 5, Jan. 1, 2011, pp. 1077-13.
Orlando A. et al. "Clinical implications of mucosal healing in the management of patients with inflammatory bowel disease", Digestive and Liver Disease2013, 45, 986-991.
Plant et al., "Association of Lacobacillus spp. with Peyer's Patches in Mice", Clinical and Diagnostic Laboratory Immunology 8: 320-324 (2001).
Polak-Berecka et al., "Physiocochemical characterization of exopolysaccharides produced by lactobacillus rhamnosus on various carbon sources", Carbohydrate Polymers, vol. 117, 2015. pp. 501-509.
Price R.D. et al. "Hyaluronic acid: the scientific and clinical evidence", Journal ofPlastic, Reconstructive & Aesthetic Surgery2007, 60: 1110-1119.
Restriction Requirement for U.S. Appl. No. 14/916,961, filed Mar. 4, 2016 on behalf of SOFAR S.P.A, dated May 10, 2019. 7 pages.
Sambrook et al. Molecular cloning: A Laboratory Manual. 3rd ed., vols. 1,2 and 3 cold Spring Harbor Laboratory Press,2001, 2100 pp.
Sanlibaba et al., "Exopolysaccharides production by lactic acid bacteria",*Applied Microbiology*, vol. 2,May 20, 2016 . . . .
Sasaki M.. et al., "Transglucosidase improves the gut microbiota profile of type 2 diabetes mellitus patients: a randomized double-blind, placebo-controlled study" *BMC Gastroenterology*, 13:81,2013.

(56) References Cited

OTHER PUBLICATIONS

Savino et al., "Laclobacillus reuteri DSM 17938 in Infantile Colic: A Randomized, Double-Blind, Placebo-Controlled Trial", Pediatrics 126: e526-e533 (2010).

Scaldaferri F. et al. "Gut microbial flora, prebiotics and probiotics in IBD: their current usage and utility", BioMed Research International2013, 9 pages.

Siew Chien Ng et al., "Effect of probiotic bacteria on the intenstinal microbiota in irritable bowel syndrome" Journal of gastroenterology and hepatology.2013.

Spiller et al., "Randomized double blind placebo-controlled trial of *Saccharomyces cerevisiae* CNCM I-3856 in irritable bowel syndrome: improvement in abdominal pain and bloating in those with predominant constipation" *United European Gastroenterology Journal.* 2016.

Stuknyte M. et al., "Potential immunomodulatory activity of bovine casein hydrolysates produced after digestion with proteinases of lactic acid bacteria" *International Dairy Journal*, 21(2011) pp. 763-769.

Taverniti and Gugliemetti et al., "The immunomodulatory properties of probiotic microorganisms beyond their viability (ghost probiotics: proposal of paraprobiotic concept)" Department of Food Science and Microbiolgy (DiSTAM), , 6:261-274(2011).

Turnbaugh et al., "The Effect of Diel on the Human Gut Microbiome: A Metagenomic Analysis in Humanized gnolobiotic Mice," Sci Transl Med: (2009).

Tursi et al., "Effect of Lactobacillus casei supplementation on the effectiveness and tolerability of a new second-line 10-day quadruple therapy after failure of a first attempt to cure Helicobacter pylori infection," Med Sci Monit 10: CR662-666 (2004).

Tursi et al., "Mesalazine and/or Lactobacillus Casei in maintaining Long-term Remission of Symptomatic Uncomplicated Diverticular Disease of the Colon" Original Paper. Hepato-Gastroenterology. 2008, 55; 916-920.

U.S. National Library of Medicine, "Effect of Lactobacillus Casei DG (Enterolactis Plus) in Patient with irritable Bowel Syndrome: a Pilot Study", ClinicalTriaals.gov,Feb. 11, 2015.

U.S. National Library of Medicine Efficacy Evaluation of a Commercial Preparation Containing Lactobacillus Casei DG on the Reduction of the Painful Symptoms Related to the Irritable Bowel Syndrome (IBS).*A Pilot Clinical Study.*Feb. 28, 2014.

Valerio et al., "Effects of Probiotic Lactobacillus paracasei-enriched Artichokes on Constipated Patients", J Clin Gastroenterol,Sep. 10, 2010.

Vernia et al. Dig. Disease Sci. (1988) 33(11): 1353-135 (Year: 1988).

Vinogradov et al., "Structural studies of the rhamnoseirch cell wall polysaccharide of lactobacillus casei BL23" *Carbohydrate Research* vol. 435,Oct. 8, 2016. pp. 156-161.

"Why VSL#3" (Obtained from https://vsl3.com/hcp/vsl-info on Aug. 22, 2017 , 4 pages.

Worthley et al. "A human, double-blind, placebo-controlled, crossover trial of prebiotic, probiotic, and symbiotic supplementation: effects on luminal, inflammatory, epigenetic, and epithelial biomarkers of colorectal cancer" (Am J Clin Nutr 2009; 90; 578-86).

Written Opinion for International Application No. PCT/IB2014/064284 filed on Sep. 5, 2014 on behalf of SOFAR SPA, dated Jan. 26, 2015. 7 pages.

Written Opinion for International Application No. PCT/IB2014/064285 filed on Sep. 5, 2014 on behalf of SOFAR SPA, dated Jan. 29, 2015. 7 pages.

Written Opinion for International Application No. PCT/IB2017/052850 filed on May 15, 2017 on behalf of SOFAR SPA, dated Aug. 17, 2017. 6 pages.

Written Opinion for International Application No. PCT/IB2017/053389 filed on Jun. 8, 2017 on behalf of SOFAR SPA, dated Oct. 6, 2017. 7 pages.

Written Opinion for International Application No. PCT/IB2017/057576 filed on Dec. 1, 2017 on behalf of SOFAR SPA, dated Feb. 22, 2018. 8 pages.

Written Opinion for International Application No. PCT/IB2017/057980 filed on Dec. 15, 2017 on behalf of SOFAR SPA, dated Mar. 19, 2018. 8 pages.

Written Opinion for International Application PCT/IB2015/052938 filed on Apr. 22, 2015 on behalf of SOFAR SPA, dated Jul. 31, 2015. 5 pages.

Zhang et al., "Isolated exopolysaccharides from lactobacillus rhamnosus GG alleviated adipogenesis mediated by TLR2 in mice" *Scientific reports*. vol. 6,Oct. 27, 2016.

Zheng, L. et al. "Regulation of colonic epithelial repair in mice by toll-like receptors and hyaluronic acid," Gastroenterology2009: 137 2041-2051.

Brussow H. "Problems with the concept of gut microbiota dysbiosis" Microbial Biotechnology, vol. 13(2), 2020, pp. 423-434.

Koebnick C. et al., "Probiotic beverage containing Lactobacillus casei Shirota improves gastrointestinal symptoms in patients with chronic constipation" Can J Gastroenterol, vol. 17 No. 11, Nov. 2003, pp. 655-658.

Non-Final Office Action for U.S. Appl. No. 14/916,959, filed Mar. 4, 2016 on behalf of SOFAR S.P.A, dated Apr. 13, 2021 33 pages.

Non-Final OfficeAction for U.S. Appl. No. 16/308,330, filed Dec. 7, 2018 on behalf ofSOFAR S.P.A, dated Apr. 30, 2021. 38 Pages.

Notice of Allowance for U.S. Appl. No. 16/301,361, filed Nov. 13, 2018 on behalf of SOFAR S.P.A, dated May 3, 2021 9 pages.

Tuohy K.M. et al., "Survivability of a probiotic Lactobacillus casei in the gastrointestinal tract of healthy human volunteers and its impact on the faecal microflora" *Journal of Applied Mircrobiology*, 2007, pp. 1026-1032.

Balzaretti S. et al., "A novel hetero-exopolysaccharide mediates the recognition of Lactobacillus paracasei DG by the immune system" Pharmabiotics Conference2015, Paris, Oct. 29-30, 2015,1 page.

Bienenstock J et al., "New insights into probiotic mechanisms" *Gut Microbes*, vol. 4 Issue 2,Apr. 2013, 7 pages.

Canadian Examination Search Report for CA Application No. 2,923,390 filed on Sep. 5, 2014 on behalf of SOFAR S.P.A, dated Jan. 26, 2021 4 pages.

Colombian Office Action for CO Application No. NC2018/0010954 filed on Nov. 1, 2018 on behalf of SOFAR S.P.A, dated Feb. 5, 2021 9 pages (Partial English + Original).

Colombian Office Action for CO Application No. NC2019/0007116 filed on Jul. 2, 2019 on behalf of SOFAR S.P.A, dated Jan. 15, 2021 19 pages (English + Original).

Declaration for the self-archiving of the doctoral thesis for "Exploring Lactobacillius Paracasei Probiosis and Metabolic Potential" by Balzaretti, Silvia Dated: Nov. 20, 2015 5 pages (English + Original).

Laws A. et al., "Determination of the structure and molecular weights of the exopolysaccharide produced by Lactobacillus acidophilus 5e2 when grown on different carbon feeds." *Carbohydr Res.*Feb. 4, 2008;343(2):301-7.

Notice of Allowance for U.S. Appl. No. 16/301,361, filed Nov. 13, 2018 on behalf of SOFAR S.P.A, dated Feb. 1, 2021 8 pages.

Paoluzi O.A., et al. "Low efficacy of levofloxacin-doxycycline-based third-line tripletherapy for Helicobacter pylori eradication in Italy." *World Journal of Gastroenterology*21: 6698-705,Jun. 2015.

Rosania R. et al. "Effect of probiotic or prebiotic supplementation on antibiotic therapy in the small intestinal bacterial overgrowth: a comparative evaluation." Curr Clin Pharmacol. May 2013;8(2):169-72. 5 pages.

Aden K. et al., "Metabolic Functions of Gut Microbes Associate with Efficacy of Tumor Necrosis Factor Antagonists in Patients with Inflammatory Bowel Diseases" Gastroenterology, 2019, pp. 1279-1292.

Allegretti J. et al., "Short Chain Fatty Acid Profiles Are Altered by Fecal Microbiota Transplantation for the Treatment of Inflammatory Bowel Disease and Recurrent Clostridioides difficile Infection" *Gastroenterology*,2019, 2 pages.

Balzaretti S. et al., "The vaginal isolate Lactobacillus paracasei LPC-S01 (DSM 26760) is suitable for oral administration" *Frontiers in Microbiology*, vol. 6, art. 952,Sep. 2015 , 13 pages.

Banasiewicz T. et al., "Determination of butyric acid dosage based on clinical and experimental studies—a literature review" *Gastroenterology Review*,2020, pp. 119-125.

(56) References Cited

OTHER PUBLICATIONS

Borren N. et al., "Alterations in Fecal Microbiomes and Serum Metabolomes of Fatigues Patients With Quiescent Inflammatory Bowel Diseases" *Clinical Gastroenterology and Hepatology*, Mar. 2020, 35 pages.
Canadian Office Action for CA Application No. 2,923,392 filed on Sep. 5, 2014 on behalf of SOFAR S.P.A, dated Jun. 1, 2020 4 pages.
Cassard L. et al, "Individual strains of Lactobacillus paracasei differentially inhibit human basophil and mouse mast cell activation," Immunity, Inflammation, and Disease vol. 4, Issue 3., 2016. 11 Pages.
Chassard C. et al., "Functional dysbiosis within the gut microbiota of patients with constipated-irritable bowel syndrome" *Alimentary Pharmacology and Therapeutics*, 2012, pp. 828-838.
Chilean Office Action for CL Application No. 201803193 filed on Sep. 5, 2014 dated Apr. 16, 2020 16 pages (English + Original).
Chinese Office Action for CN Application No. 201480049288 filed on Sep. 5, 2014 on behalf of SOFAR S.P.A, dated Sep. 16, 2020 8 pages (English + Original).
Colombian Office Action for CO Application No. NC2018/0010950 filed on Sep. 5, 2014 on behalf of SOFAR S.P.A, dated Jul. 27, 2020 11 pages (Partial English + Original).
Compare D. et al., "Lactobacillus casei DG and its postbiotic reduce the inflammatory mucosal response: an ex-vivo organ culture model of post-infectious irritable bowel syndrome" *BMC Gastroenterology*, 2017, 8 pages.
Costalos et al., "Enteral feeding of premature infants with *Saccharomyces boulardii*" *Early Human Development*, 74,(2003), 89-96.
Cremon C. et al., "Effect of Lactobacillus paracasei CNCM I-1572 on symptoms, gut microbiota, short chain fatty acids, and immune activation in patients with irritable bowel syndrome: A pilot randomized clinical trial" *UEG Journal*, Sep. 2017, 10 pages.
Eurasian Notification of Grant for Application No. 201690464/28 filed on Sep. 5, 2014 on behalf of SOFAR S.P.A, dated Jun. 9, 2020 2 pages (English + Original).
Final Office Action for U.S. Appl. No. 14/916,959, filed Mar. 4, 2016 on behalf of SOFAR S.P.A, dated Aug. 21, 2020 48 pages.
Final Office Action for U.S. Appl. No. 15/305,470, filed Oct. 20, 2016 on behalf of SOFAR S.P.A, dated Jul. 10, 2020 21 pages.
Final Office Action for U.S. Appl. No. 16/301,361, filed Nov. 13, 2018 on behalf of SOFAR S.P.A, dated Sep. 21, 2020 11 pages.
Gargari G. et al., "Fecal Clostridiales distribution and short-chain fatty acids reflect bowel habits in irritable bowel syndrome" Environmental Microbiology, Sep. 2018, 31 pages.
Hustoft T. et al., "Effects of varying dietary content of fermentable short-chain carbohydrates on symptoms, fecal microenvironment, and cytokine profiles in patients with irritable bowel syndrome" Neurogastroenterology & Motility, Sep. 2016, 9 pages.
Irritable Bowel Syndrome—Wikipedia, dated Sep. 16, 2020. 33 pages, https://en.wikipedia.org/wiki/Irritable_bowel_syndrome.
Israeli Office Action for Application No. 244391 filed on Mar. 2, 2016 on behalf of SOFAR S.P.A, dated Jun. 24, 2020 4 pages (English + Original).
Israeli Office Action for Application No. 269107 filed on Sep. 3, 2019 on behalf of SOFAR S.P.A, dated May 17, 2020 5 pages (English + Original).
Japanese Office Action for JP Application No. 2016564193 filed on Apr. 22, 2015 on behalf of SOFAR S.P.A, dated Feb. 18, 2020 11 pages (English + Original).
Langhorst J. et al., "Distinct patterns of short-chain fatty acids during flare in patients with ulcerative colitis under treatment with mesalamine or a herbal combination of myrrh, chamomile flowers, and coffee charcoal: secondary analysis of a randomized controlled trial" European Journal of Gastroenterology & Hepatology, Feb. 2020, 6 pages.
Magnusson M. et al., "The Anti-inflammatory Immune Regulation Induced by Butyrate is Impaired in Inflamed Intestinal Mucosa from Patients with Ulcerative Colitis" Inflammation, Apr. 2020, 11 pages.
Mcfarland, et al., "Strain-Specificity and Disease-Specificity of Probiotic Efficacy: A Systematic Review and Meta-Analysis," Frontiers in Medicine, May 7, 2018. 14 Pages.
Mexican Office Action for MX Application No. MX/a/2016/002766 filed on Sep. 5, 2014 on behalf of SOFAR S.P.A, dated Aug. 13, 2020 10 pages (English + Original).
Pituch A. et al., "Butyric acid in functional constipation" *Przeglad Gastroenterologiczny*,2013, 4 pages.
Pozuelo M. et al., "Reduction of butyrate and methane producing microorganisms in patients with Irritable Bowel Syndrome" *Nature Scientific Reports*, Apr. 2015, 12 pages.
Ralf Jager et al., "Probiotic Administration Increases Amino Acid Absorption from Plant Protein: a Placebo-Controlled, Randomized, Double-Blind, Multicenter, Crossover Study," Probiotics and Antimicrobial Proteins, 2020. 10 Pages.
Ringel-Kulka T. et al., "Short Chain Fatty Acids and Intestinal Transit in Patients With Irritable Bowel Syndrome and Healthy Controls" *AGA Abstracts*, May 2012, 1 page.
Scarpellini E. et al., "Efficacy of butyrate in the treatment of diarrhea-predominant irritable bowel syndrome" Digestive and Liver Disease, 2007, 4 pages.
Shi Y. et al., "Function and clinical implications of short-chain fatty acids in patients with mixed refractory constipation" Association of Coloproctology of Great Britain and Ireland, Feb. 2016, 8 pages.
Smokvina T. et al "Lactobacillus paracasei Comparative Genomics: Towards Species Pan-Genome Definition and Exploitation of Diversity," PLOS ONE, Jul. 19, 2013. 16 Pages.
Sun Q. et al., "Alterations in fecal short-chain fatty acids in patients with irritable bowel syndrome" *Systematic Review and Meta-Analysis*, Jan. 2019, 12 pages.
Third Chinese Office Action for CN Application No. 201480049296.4 filed on Sep. 5, 2014 on behalf of SOFAR S.P.A, dated Mar. 18, 2020 13 pages (English + Original).
Turco F. et al., Bacterial stimuli activate nitric oxide colonic mucosal production in diverticular disease. Protective effects of L. casei DG (Lactobacillus paracasei CNCM I-1572) UEG Journal, Nov. 2016, 10 pages.
Turco F. et al., "Enteroglial-derived S100B protein integrates bacteria-induced Toll-like receptor signalling in human enteric glial cells" GUT Neurogastroenterology, vol. 63, Mar. 2014, Originally Published online Jan. 3, 2013, 12 pages.
Tursi A. et al., "Assessment of Fecal Microbiota and Fecal Metabolome in Symptomatic Uncomplicated Diverticular Disease of the Colon" *J. Clin Gastroenterol*, Oct. 2016, 4 pages.
Tursi A. et al., "Fecal Microbiota, Fecal and Urinary Metabolic Profiling and Symptomatic Uncomplicated Diverticular Disease of the Colon" *Digestive and Liver Disease*, 2017, 1 page.
Tursi A. et al., "Natural History of Symptomatic Uncomplicated Diverticular Disease: A 13-Year Prospective Study" *AGA Abstracts*, Apr. 2017, 1 page.
Zhuang M. et al., "Abundance of probiotics and butyrate-production microbiome manages constipation via short-chain fatty acids production and hormones secretion" Molecular Nutrition & Food Research, Jul. 2019, 41 pages.
Zhuang M. et al., "Systematic Review and Meta-analysis: Short-Chain Fatty Acid Characterization in Patients With Inflammatory Bowel Disease" *Inflammatory Bowel Disease*, Nov. 2019, 13 pages.
Azad M.D.A.K et al., "Immunomodulatory Effects of Probiotics on Cytokine Profiles" Biomed Research International, vol. 2018, Article ID 8063647, Oct. 2018, pp. 1-10.
Bedford A. et al., "Implications of butyrate and its derivatives for gut health and animal production" *Animal Nutrition*, vol. 4, 2018, pp. 151-159.
Borycka-Kiciak K. et al., "Butyric acid—a well-known molecule revisited" *Gastroenterology Rev*, vol. 12 No. 2, 2017, pp. 83-89.
Canadian Office Action for CA Application No. 2,923,390 filed on Sep. 5, 2014 on behalf of SOFAR S.P.A, dated Nov. 29, 2021 5 pages.
Cheng A. et al., "Polyphenols from blueberries modulate inflammation cytokines in LPS-induced RAW264.7 macrophages", *International Journal of Biological Macromolecules*, Elsevier vol. 69, Jun. 2014, pp. 382-387.

(56) References Cited

OTHER PUBLICATIONS

Chinese Office Action for CN Application No. 201780029401.1 filed on May 15, 2017 on behalf of SOFAR S.P.A, dated Dec. 15, 2021 (English + Original) 20 pages.
Cicenia, A. et al., "Postbiotic Activities of Lactobacilli-derived Factors", J Clin Gastroenterol, vol. 48, Supp. 1, Nov./Dec. 2014, S18-S22 (5 pages).
Colombian Office Action for CO Application No. NC2018/0010950 filed on May 15, 2017 on behalf of SOFAR S.P.A, dated Oct. 14, 2021 (Partial English + Original) 9 pages.
Connors J. et al., "The Role of Succinate in the Regulation of Intestinal Inflammation" *Nutrients*, vol. 11 No. 25, 2019, 12 pages.
Corrected Notice of Allowability for U.S. Appl. No. 15/305,470, filed Oct. 20, 2016, on behalf of SOFAR SPA, dated Feb. 25, 2022. 3 Pages.
Corrected Notice of Allowability for U.S. Appl. No. 15/305,470, filed Oct. 20, 2016 on behalf of SOFAR S.P.A, dated Jan. 10, 2022 4 pages.
Cui J. et al., "NMR-based metabonomics and correlation analysis reveal potential biomarkers associated with chronic atrophic gastritis" *Journal of Pharmaceutical and Biomedical Analysis*, vol. 132, 2017, pp. 77-86.
Feng W. et al., "Sodium Butyrate Attenuates Diarrhea in Weaned Piglets and Promotes Tight Junction Protein Expression in Colon in a GPR109A-Dependent Manner" *Cellular Physiology and Biochemistry*, vol. 47, 2018, pp. 1617-1629.
Final Office Action for U.S. Appl. No. 16/308,330, filed Dec. 7, 2018, on behalf of SOFAR S.P.A, dated Feb. 9, 2022. 22 Pages.
Final Office Action for U.S. Appl. No. 14/916,959, filed Mar. 4, 2016 on behalf of SOFAR S.P.A, dated Dec. 29, 2021. 29 Pages.
Fiorino et al., "P325 Efficacy and Safety of IBD98E, a Sodium Hyaluronate Topical Preparation, in the Induction of Clinical and Endoscopic Remission in Patients with Distal Ulcerative Colitis: An Open Label Pilot Study," *United European GastroenterologyJournal*: 1(1S) (A219). Oct. 2013.
Gwiazdowska D. et al., "The impact of polyphenols on Bifidobacterium growth", Acta Biochimica Polonica, vol. 62 No. 4, *Jan. 2015*, 895-901. 8 pages.
Hajjar R. et al., "The role of butyrate in surgical and oncological outcomes in colorectal cancer" *American Journal of Physiology*, vol. 320, Jan. 2021, pp. G601-G608.
Hakansson A. et al., "Blueberry husks, rye bran and multi-strain probiotics affect the severity of colitis induced by dextran sulphate sodium" *Scandinavian Journal of Gastroenterology*, vol. 44 No. 10, Jan. 2009, pp. 1213-1225.
Hurst N.R. et al., "The Short Chain Fatty Acids, butyrate and Propionate, have Differential Effects on the Motility of the Guinea Pig Colon" *Neurogastroenterol Motil.*, vol. 26 No. 11, Nov. 2014, pp. 1586-1596.
International Preliminary Report on Patentability for International Application No. PCT/IB2020/058774 filed on Sep. 21, 2020 on behalf of SOFAR S.P.A, dated Mar. 15, 2022 16 pages.
International Preliminary Report on Patentability for International Application No. PCT/IB2020/058769 filed on Sep. 21, 2020 on behalf of SOFAR S.P.A, dated Mar. 15, 2022 6 pages.
International Preliminary Report on Patentability for International Application No. PCT/IB2020/058777 filed on Sep. 21, 2020 on behalf of SOFAR S.P.A, dated Mar. 15, 2022 6 pages.
International Preliminary Report on Patentability for International Application No. PCT/IB2020/058778 filed on Sep. 21, 2020 on behalf of SOFAR S.P.A, dated Mar. 15, 2022 6 pages.
International Preliminary Report on Patentability for International Application No. PCT/IB2020/060412 filed on Nov. 5, 2020 on behalf of SOFAR S.P.A, dated May 10, 2022 7 pages.
International Search Report and Written Opinion for International Application No. PCT/IB2020/058778 filed on Sep. 21, 2020 on behalf of SOFAR S.P.A, dated Feb. 18, 2021 8 pages.
International Search Report and Written Opinion for International Application No. PCT/IB2020/058774 filed on Sep. 21, 2020 on behalf of SOFAR S.P.A, dated Dec. 8, 2020 8 pages.

International Search Report and Written Opinion for International Application No. PCT/IB2020/058777 filed on Sep. 21, 2020 on behalf of SOFAR S.P.A, dated Apr. 20, 2021 26 pages.
International Search Report and Written Opinion for International Application No. PCT/IB2020/060412 filed on Nov. 5, 2020 on behalf of SOFAR S.P.A, dated Mar. 4, 2021 10 pages.
Koradia P. et al., "Probiotic and cranberry supplementation for preventing recurrent uncomplicated urinary tract infections in pre-menopausal women: a controlled pilot study" *Expert Review of Anti-Infective Therapy*, vol. 17 No. 9, Sep. 2019, pp. 733-740.
Krokowicz L. et al., "Sodium butyrate and short chain fatty acids in prevention of travellers, diarrhoea—a randomized prospective study" *Travel Medicine and Infectious Disease*, Aug. 2013, 17 pages.
Lacombe A. et al., "The potential of berries to serve as selective inhibitors of pathogens and promoters of beneficial microorganisms" *Food Quality and Safety*, vol. 1 No. 1, Mar. 2017, pp. 3-12.
Le Noci V. et al., "Modulation of Pulmonary Microbiota by Antibiotic or Probiotic Aerosol Therapy: A Strategy to Promote Immunosurveillance against Lung Metastases" *Cell Reports*, vol. 24 No. 13, Sep. 2018, pp. 3528-3538.
Mexican Office Action for MX Application No. MX/a/2016/002766 filed on Sep. 5, 2014 on behalf of SOFAR S.P.A, dated Sep. 6, 2021. 12 pages (English + Original).
Mileo A.M et al., "Polyphenols: Immunomodulatory and Therapeutic Implication in Colorectal Cancer" *Frontiers in Immunology*, vol. 10, article 729 Apr. 2019, 10 pages.
Milko Radicioni, et al., "Survival of L. casei DG (CNCMI1572) in the gastrointestinal tract of a healthy paediatric population", *European Journal of Nutrition, Steinkopff Verlag*, vol. 58 No. 8, Nov. 2018, 3161-3170. 10 pages.
Nanau R.M. et al., "Nutritional and Probiotic Supplementation in Colitis Models" *Digestive Diseases and Sciences, Kluwer Academic Publishers—Plenum Publishers*, vol. 57 No. 11, Jun. 2012, pp. 2786-2810.
Non-Final Office Action for U.S. Appl. No. 17/090,669, filed Nov. 5, 2020, on behalf of SOFAR S.P.A, dated Feb. 17, 2022. 45 Pages.
Notice of Allowance for U.S. Appl. No. 15/305,470, filed Oct. 20, 2016 on behalf of SOFAR S.P.A, dated Feb. 15, 2022 6 pages.
Notice of Allowance for U.S. Appl. No. 15/305,470, filed Oct. 20, 2016, on behalf of SOFAR SPA, dated Jun. 9, 2022. 11 Pages.
Notice of Allowance for U.S. Appl. No. 16/301,361, filed Nov. 13, 2018, on behalf of SOFAR S.P.A, dated Mar. 30, 2022. 11 Pages.
Notice of Allowance for U.S. Appl. No. 16/465,237, filed May 30, 2019, on behalf of SOFAR S.P.A, dated Jun. 1, 2022. 15 Pages.
Patel, R., et a., "New Approaches for Bacteriotherapy: Prebiotics, New-Generation Probiotics, and Synbiotics," *Clinical Infectious Diseases*, vol. 60, Issue supplement 2, May 15, 2015. pp. S108-S121. 15 Pages. https://doi.org/10.1093/cid/civ177.
Rajendran V.M. et al., "Na—H Exchanger Isoform-2 (NHE2) Mediates Butyrate-dependent Na+ Absorption in Dextran Sulfate Sodium (DSS)-induced Colitis" *Journal of Biological Chemistry*, vol. 290 No. 42, Oct. 2015, 25487-25496. 10 pages.
Saez-Lara M.J. et al., "The Role of Probiotic Lactic Acid Bacteria and Bifidobacteria in the Prevention and Treatment of Inflammatory Bowel Disease and Other Related Diseases: A systematic review of randomized human clinical trials" *Biomed Research International*, vol. 2015, article ID 505878 Jan. 2015, pp. 1-15.
Tsilingiri, K. et al., "Probiotic and postbiotic activity in health and disease: activity comparison on a novel polarised ex-vivo organ culture method", Gut 2012; 61:1007-1015 (9 pages).
Vicariotto, Franco "Effectiveness of an association of a cranberry dry extract, D-mannose, and the two microorganisms Lactobacillus plantarum LP01 and Lactobacillus paracasei LPC09 in women affected by cystitis: a pilot study." *J Clin Gastroenterol*, Nov. 2014, vol. 48, Supp. 1,: S96-S101. 6 pages.
Xu J. et al., "Intake of blueberry fermented by lactobacillus plantarum affects the guy microbiota of L-name treated rats" *Evidence-Based Complementary and Alternative Medicine*, vol. 2013, article ID 809128, Jan. 2013, pp. 1-9.
Xue H. Lactose-Induced Chronic Diarrhea Results from Abnormal Luminal Microbial Fermentation and Disorder of Ion Transport in the Colon *Frontiers in Physiology*, vol. 11, article 877, Jul. 2020, pp. 1-14.

(56) References Cited

OTHER PUBLICATIONS

Yehua Yan, et al., "Mixed fermentation of blueberry pomace with L. rhamnosus GG and L. plantarum-1: Enhance the active ingredient, antioxidant activity and health-promoting benefits", *Food and Chemical Toxicology*, vol. 131, 2019, 8 pages.

Yoshida Y. et al., "Oral administration of Lactobacillus plantarum Lq80 and Megasphaera elsdenii iNP-001 induces efficient recovery from mucosal atrophy in the small and the large intestines of weaning piglets" *Animal Science Journal*, vol. 80, 2009, pp. 709-715.

Yuanning Su, et al., "Analysis of protein degradation and aroma-producing capacity of lactic aced bacteria" Chinese Brewing, vol. 33 No. 3, Dec. 31, 2014 (English Abstract + Original) 36-39. 4 pages.

Brunkwall L. et al., "Self-reported bowel symptoms are associated with differences in overall gut microbiota composition and enrichment of Blautia in a population-based cohort" *Journal of Gastroenterology and Hepatology*, vol. 36, (2021), pp. 174-180.

Corrected Notice of Allowability for U.S. Appl. No. 16/465,237, filed May 30, 2019, on behalf of SOFAR S.P.A. dated Jun. 22, 2022. 20 Pages.

Cure—Wikipedia, the free encyclopedia. Date: May 12, 2013 4 pages https://web.archive.org/web/20130512085159/https:en.wikipedia.org/wiki/Remission_(medicine).

De Almada C. N. et al., "Paraprobiotics: Evidences on their ability to modify biological responses, inactivation methods and perspectives on their application in foods" *Trends in Food Science & Technology*, vol. 58, 2016, pp. 96-114.

Final Office Action for U.S. Appl. No. 17/090,669, filed Nov. 5, 2020 on behalf of SOFAR S.P.A., dated Nov. 9, 2022. (15 pages).

Lee Y. K. et al., "Handbook or Probiotices and Prebiotics" Wiley, 2009, Excerpt: 3 pages.

Metagenomics—Wikipedia, the free encyclopedia, Dated: May 16, 2013 https://web.archive.org/web/20130516095714/https://en.wikipedia.org/Metagenomics, 16 pages.

Non-Final OA Office Action for U.S. Appl. No. 16/308,330, filed Dec. 7, 2018, on behalf of SOFAR S.P.A. dated Sep. 1, 2022. 26 Pages.

Non-Final Office Action for U.S. Appl. No. 14/916,959, filed Mar. 4, 2016, on behalf of SOFAR S.P.A. dated Sep. 30, 2022. 34 Pages.

Non-Final Office Action for U.S. Appl. No. 14/916,961, filed Mar. 4, 2016 on behalf of SOFAR S.P.A. dated Aug. 29, 2022. 25 Pages.

Notice of Allowance for U.S. Appl. No. 16/465,237, filed May 30, 2019 on behalf of SOFAR S.P.A. dated Nov. 2, 2022 13 pages.

Patel R. M. et al., "Therapeutic Use of Prebiotics, Probiotics, and Postbiotics to Prevent Necrotizing Enterocolitis: What is the Current Evidence?" *Clin Perinatol*, vol. 40, Mar. 2013, pp. 1-20.

Poortmans J. R. et al., "Protein metabolism and physical training: any need for amino acid supplementation?" *Nutrire*, vol. 41 No. 21, 2016, pp. 1-17.

Qin J. et al., "A human gut microbial gene catalogue established by metagenomic sequencing" *Nature*, vol. 46, Mar. 2010, pp. 59-67.

Santigosa E. et al., "Modifications of intestinal nutrient absorption in response to dietary fish meal replacement by plant protein sources in sea bream (Sparus aurata) and rainbow trout (Onchorynchus mykiss)" *Fish Nutrition Research Laboratory*, 2011, 38 pages.

Tomar S. K. et al., "Role of probiotics, prebiotics, synbiotics, and postbiotics in inhibition of pathogens" *The Battle Against Microbial Pathogens: Basic Science, Technological Advances and Educational Programs*, 2015, pp. 717-732.

Tsilingiri K. et al., "Postbiotics: what else?" *Beneficial Microbes*, vol. 4 No. 1, Mar. 2013, pp. 101-107 (Abstract Only).

WHO Technical Report Series 935—Protein And Amino Acid Requirements in Human Nutrition, 2007, 284 pages.

Zhernakova A. et al., "Population-based metagenomics analysis reveals markers for gut microbiome composition and diversity" Science, vol. 352, Apr. 2016, 15 pages.

Final Office Action for U.S. Appl. No. 14/916,961, filed Mar. 4, 2016 on behalf SOFAR S.P.A., dated Dec. 19, 2022, 19 pages.

Tursi et al., "Mesalazine and/or Lactobacillus casei in preventing recurrence of symptomatic uncomplicated diverticular disease of the colon: A Prospective, randomized, open-label study", Journal of Clinical Gastroenterol, Raven Press Ltd, NY New York. vol. 40, No. 2, Apr. 1, 2006. pp. 312-316.

Response to Final Office Action (Submission with RCE) for U.S. Appl. No. 14/916,961, filed Mar. 4, 2016 on behalf SOFAR S.P.A., Response filed on May 19, 2023. 13 pages.

Notice of Allowance for U.S. Appl. No. 14/916,961, filed Mar. 4, 2016 on behalf SOFAR S.P.A., dated Jul. 24, 2023, 13 pages.

Annex to Summons for EP Application No. 17 742 849.7 filed on Jun. 8, 2017 on behalf of SOFAR S.P.A., Mail Date: Feb. 23, 2023, 8 pages.

Annibale, B. et al., "Efficacy of *Lactobacillus paracasei* sub. paracasei F19 on abdominal symptoms in patients with symptomatic uncomplicated diverticular disease: A pilot study", Minerva Gastroentrologica E Dietologica, vol. 57, No. 1, Mar. 2011, 12 pages.

Arumugam, M., et al., "Enterotypes of the human gut microbiome," *Nature* 473: 174-180. May 12, 2011. 16 Pages. https://doi.org/10.1038/nature09944.

Brazilian Office Action for BR112018074795 filed on Jun. 8, 2017 on behalf of SOFAR S.P.A. dated Sep. 22, 2022 6 pages (Partial English Translation + Original).

Canadian Office Action for CA Application No. 2,923,390 filed on Mar. 4, 2016 on behalf of SOFAR S.P.A. dated Nov. 3, 2022, 4 pages.

Colombian Office Action for NC2018/0010954 filed on Nov. 1, 2018 on behalf of SOFAR S.P.A. dated Jan. 6, 2022 (English Translation + Original) 8 pages.

Corrected Notice of Allowability for U.S. Appl. No. 16/308,330, filed Dec. 7, 2018 on behalf of SOFAR S.P.A., dated Feb. 3, 2023. (6 pages).

Corrected Notice of Allowability for U.S. Appl. No. 17/090,669, filed Nov. 5, 2020 on behalf of SOFAR S.P.A., dated May 1, 2023. (2 pages).

Corrected Notice of Allowability for U.S. Appl. No. 17/090,669, filed Nov. 5, 2020 on behalf of SOFAR S.P.A., dated May 17, 2023. (3 pages).

Distrutti, Eleanora et al., "Gut microbiota role in irritable bowel syndrome: New therapeutic strategies", World J Gastroenterol, Feb. 2, 20161, 22(7), 2219-2241 (24 pages).

Final Office Action for U.S. Appl. No. 14/916,959, filed Mar. 4, 2016 on behalf of SOFAR S.P.A., dated Mar. 27, 2023 (31 pages).

Hamady, M., et al., "Microbial community profiling for human microbiome projects: Tools, techniques, and challenges," Genome Res. 19: 1141-1152. Apr. 21, 2009. 12 Pages. doi:10.1101/gr.085464.108.

Health—Wikipedia, the free encyclopedia. Dated Aug. 28, 2013 through the wayback machine. 8 pages.

Healthy Definition and Meaning—Merriam-Webster Dictionary, downloaded Feb. 19, 2023, https://www.merriam-webster.com/dictionary/healthy, 16 pages.

International Search Report and Written Opinion for International Application No. PCT/IB2020/058769 filed on Sep. 21, 2020 on behalf of SOFAR S.P.A. dated Feb. 18, 2021 8 pages.

Kim, H.J. et al., "A randomized controlled trial of a probiotic combination VSL# 3 and placebo in irritable bowel syndrome with bloating", Neurogastroenterol Motil, Oct. 2005, 17(5), 687-696, (10 pages).

Lamiki, Pepu et al., "Probiotics in Diverticular Disease of the Colon: an Open Label Study", J. Gastrointestin Liaver Dis, Mar. 2010, Vo. 19, No. 1, pp. 31-36. (6 pages).

Maria Jose Saez-Lara et al., "The Role of Probiotic Lactic Acid Bacteria and Bifidobacteria in the Prevention and Treatment of Inflammatory Bowel Disease and Other Related Diseases: A Systematic Review of Randomized Human Clinical Trials", Biomed Research International, vol. 2015, Jan. 1, 2015 (Jan. 1, 2015), p. 1-15, 16 pages (XP055677451).

Mayo Clinic, "Diabetic neuropathy", Mayo Foundation for Medical Education and Research, 2022, downloaded from https://www.mayoclinic.org/diseases-conditions/diabetic-neuropathy/symptoms-causes/syc-20371580 , 3 pages.

(56) References Cited

OTHER PUBLICATIONS

Notice of Allowance for U.S. Appl. No. 16/308,330, filed Dec. 7, 2018 on behalf of SOFAR S.P.A., dated Jan. 25, 2023. (11 pages).
Notice of Allowance for U.S. Appl. No. 16/308,330, filed Dec. 7, 2018 on behalf of SOFAR S.P.A., dated May 11, 2023. (9 pages).
Notice of Allowance for U.S. Appl. No. 17/090,669, filed Nov. 5, 2020 on behalf of SOFAR S.P.A., dated Apr. 24, 2023. (7 pages).
Riesenfeld, C.S., "Metagenomics: Genomic Analysis of Microbial Communities," *Annu. Rev. Genet.* 38: 525-52. Jul. 14, 2004. 30 Pages. doi: 10.1146/annurev.genet.38.072902.091216.
Summons to attend oral proceedings pursuant to Rule 115(1) EPC for EP Application No. 17 742 849.7 filed on Jun. 8, 2017 on behalf of SOFAR S.P.A., Mail Date: Feb. 23, 2023, 2 pages.
U.S. National Library of Medicine, "Efficacy Evaluation of a Commercial Preparation Containing Lactobacillus Casei DG on the Reduction of the Painful Symptoms Related to the Irritable Bowel Syndrome (IBS). A Pilot Clinical Study", ClinicalTrials.gov, (Feb. 28, 2014), Dated: Feb. 28, 2014. 7 pages. Wesite: clinicaltrials.gov/show/NCT02077699, (Jan. 26, 2017), XP055339147.
U.S. National Library of Medicine Efficacy Evaluation of a Commercial Preparation Containing Lactobacillus Casei DG on the Reduction of the Painful Symptoms Related to the Irritable Bowel Syndrome (IBS). A Pilot Clinical Study. Downloaded Nov. 27, 2019. Last Updated: Dec. 2, 2014. 7 pages. (D2).
U.S. National Library of Medicine, Search of: "accepts healthy volunteers"-List Results, ClinicalTrials.gov, downloaded Feb. 19, 2023, https://clinicaltrials.gov/ct2/results?cond=&term=healthy&cntry=&sta. 4 pages.
Valentino Le Noci et al., "Modulation of Pulmonary Microbiota by Antibiotic or Probiotic Aerosol Therapy: A Strategy to Promote Immunosurveillance against Lung Metastases", Cell Reports, vol. 24, No. 13, Sep. 25, 2018 (Sep. 25, 2018), p. 3528-3538, 12 pages (XP055676264).
Xu, J., "Microbial ecology in the age of genomics and metagenomics: concepts, tools, and recent advances" Molecular Ecology, Jun. 2006, 15(7), 1713-1731 (19 pages).
Yu, K., et al., "Metagenomic and Metatranscriptomic Analysis of Microbial Community Structure and Gene Expression of Activated Sludge," *PLoS One* 7(5): e38183. May 2012. 13 Pages. https://doi.org/10.1371/journal.pone.0038183.

PROBIOTICS FOR USE IN THE TREATMENT OF DIVERTICULOSIS AND DIVERTICULAR DISEASE

CROSS-REFERENCE TO RELATED APPLICATIONS

This application is a 371 national-stage application of International PCT Application No. PCT/IB2017/057980, filed Dec. 15, 2017, which claims priority to Italian Patent Application No. 102016000127498, filed Dec. 16, 2016.

DESCRIPTION

The present invention relates to the use of probiotics to control the inflammatory process of the colon in subjects with structural modifications of the colon wall, preferably in subjects with diverticulosis, preferably affected by diverticular disease.

PRIOR ART

Colonic diverticulosis is the most frequent anatomical alteration of the colon, often detected during colonoscopy. It refers to structural modifications of the colon wall, which appears to be characterised by the presence of pouches called diverticula.

Although the majority of people with colonic diverticulosis remain asymptomatic, about 20% of patients develop symptoms. This condition is defined as diverticular disease.

A situation in which there are persistent abdominal symptoms attributed to diverticula in the absence of macroscopically manifest colitis or diverticulitis is defined as symptomatic uncomplicated diverticular disease.

Diverticulitis, by contrast, is an acute macroscopic inflammation of the diverticula, which may be simple or complicated, depending on whether or not characteristics of complications such as abscesses, peritonitis, obstruction, fistulas or haemorrhaging are observed on computed tomography.

The pathological mechanisms causing the formation of colonic diverticula still remain unclear. These formations are probably the result of complex interactions between diet, intestinal microbiota, genetic factors, colon motility and microscopic inflammation. All of these factors must also be considered as potential targets of the diverticular disease treatment.

Among them, the alteration of intestinal microbiota might have an important role. Recently, in fact, a variety of preliminary information has been made available regarding the impact of modifications of the microbial population in subjects with diverticular disease, which could be the cause of a process of dysbiosis such as to favour the development of several symptoms and which, at the same time, could predispose them to an episode of diverticulitis.

In recent years, moreover, numerous findings have suggested a significant role of inflammation in determining the symptoms and in the development of complications.

In fact, it has been observed that diverticular disease has a significant microscopic inflammatory infiltrate. This microscopic inflammation, which ranges from a greater chronic lymphocyte infiltration to an active neutrophile infiltrate, seems to be tied to the severity of the disease.

Furthermore, diverticular disease shows a greater expression of pro-inflammatory cytokines such as TNFα. Persistent inflammation, both endoscopic and histological, has recently been identified as a significant risk factor for the recurrence of diverticulitis.

In light of the foregoing, there is an extremely felt need to identify products that make it possible to control the inflammatory process at the level of the colon, in particular to prevent/control/treat diverticular disease and its symptoms and to prevent the complications thereof.

The Applicant has found the use of probiotics based on bacteria and/or yeast and/or other microorganisms as a solution to the above-described needs. In particular, the present solution proposes the use of bacteria belonging to the genus *Lactobacillus* and/or *Bifidobacterium*, preferably the bacterial species *Lactobacillus paracasei*.

In fact, following the administration of the probiotics, as described below in detail, one observes a down-regulation of iNOS expression, pro-inflammatory cytokines and NO release in healthy subjects and above all in subjects affected by various forms of diverticulosis undergoing stimulation/treatment with pathogenic bacteria such as enteroinvasive *E. coli*. Therefore, the administration of probiotics, in particular based on bacteria belonging to the genus *Lactobacillus* and/or *Bifidobacterium*, preferably the bacterial species *Lactobacillus paracasei*, has shown to be effective in the treatment and/or prevention of the various forms of diverticular disease and/or the symptoms associated therewith.

DESCRIPTION OF THE FIGURES

The present invention will be described in detail below, also with the aid of the following figures and with examples that are not intended to have any limiting character.

In particular.

DETAILED DESCRIPTION

Figure 1:
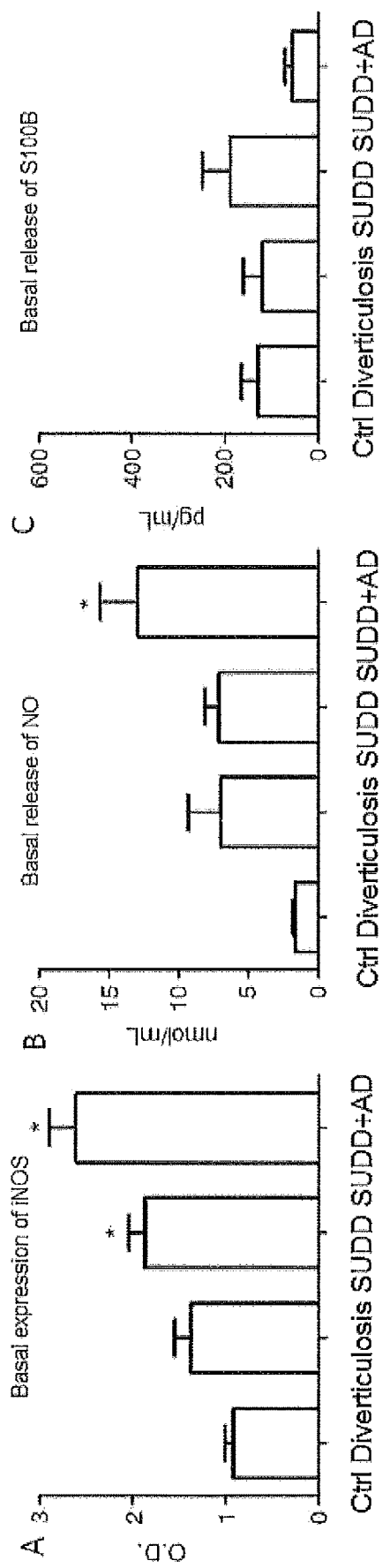
FIG. 1 shows the basal levels of iNOS expression and the release of NO and S100B in the collected samples (Control, Diverticulosis, SUDD, SUDD+AD).

A first aspect of the present invention relates to the use of probiotics for the treatment and/or prevention and/or improvement of the symptoms associated with diverticulosis, in particular diverticular disease. The diverticular disease is preferably symptomatic uncomplicated diverticular disease (SUDD), or segmental colitis associated with diverticulosis (SCAD). Diverticulosis, associated with symptomatic or asymptomatic diverticular disease, to which in general the present invention makes reference, is associated with an over-expression of NO and/or iNOS and/or at least one pro-inflammatory cytokine, preferably selected from TNFα, IL1β, IL-6b, IL-10 and combinations thereof. For the purposes of the present invention, the probiotics can be taken as an adjuvant to any therapy designed to treat or prevent diverticulosis and the preferred forms described above, i.e. taking probiotics, preferably on a regular basis as described in greater detail below, shows to favour a positive outcome of the presently available treatments designed to treat and/or prevent this pathology in its different forms. Therefore, the use of probiotics aimed at treating and/or preventing and/or improving the symptoms associated with diverticulosis, in particular, asymptomatic diverticulosis and/or diverticular disease, may be associated or combined with further therapeutic approaches, preferably of a pharmacological or socio-behavioural type, for example a healthy lifestyle or diet.

In this context, the definition of "probiotic" is the one formulated by a group of experts jointly convened in 2001 by the FAO and the WHO: "Live microorganisms which when administered in adequate amounts confer a health benefit on the host". In particular, in Italy, the Ministry of Health has defined probiotics as "microorganisms which demonstrate to be able, once ingested in sufficient amounts, to exert functions that are beneficial for the body", substantially echoing the definition of the two above-mentioned organisations.

The probiotics to which the present invention relates are based on bacteria and/or yeast and/or other microorganisms.

According to a preferred aspect of the present invention, the bacteria preferably belong to a genus selected from: Lactobacillus, Bifidobacterium, Bacillus, Propionibacterium, Streptococcus, Lactococcus, Aerococcus, Enterococcus and combinations thereof. The genus that is preferred for the purposes of the present invention is Lactobacillus and/or Bifidobacterium.

According to a further preferred aspect of the invention, the bacteria of the genus Lactobacillus belong to at least one of the following species: Lactobacillus paracasei, Lactobacillus acidophilus, Lactobacillus rhamnosus, Lactobacillus amylolyticus, Lactobacillus amylovorus, Lactobacillus alimentarius, Lactobacillus aviaries, Lactobacillus brevis, Lactobacillus buchneri, Lactobacillus casei, Lactobacillus cellobiosus, Lactobacillus coryniformis, Lactobacillus crispatus, Lactobacillus curvatus, Lactobacillus delbrueckii, Lactobacillus farciminis, Lactobacillus fermentum, Lactobacillus gallinarum, Lactobacillus gasseri, Lactobacillus helveticus, Lactobacillus hilgardii, Lactobacillus johnsonii, Lactobacillus kefiranofaciens, Lactobacillus kefiri, Lactobacillus mucosae, Lactobacillus panis, Lactobacillus coffinoides, Lactobacillus paraplantarum, Lactobacillus pentosus, Lactobacillus plantarum, Lactobacillus pontis, Lactobacillus reuteri, Lactobacillus sakei, Lactobacillus salivarius and Lactobacillus sanfranciscensis.

Particularly preferred for the purposes of the present invention is the bacterial species Lactobacillus paracasei, preferably the strain DG® (Lactobacillus paracasei CNCM I-1572).

The bacterial strain L. casei DG® (Lactobacillus paracasei CNCM I1572) was deposited by SOFAR S.p.A. with the National Collection of Microorganism Cultures of the Pasteur Institute of Paris on May 5, 1995, with the deposit number CNCM I-1572.

According to a further preferred aspect of the invention, the bacteria of the Bifidobacterium genus belong to at least one of the following species: B. animalis, B. bifidum, B. breve, B. infantis, B. longum, B. adolescentis, B. catenulatum, B. angulatum, B. asteroides, B. bourn, B. choerinum, B. coryneforme, B. cuniculi, B. denticolens, B. dentium, B. gallicum, B. gallinarum, B. indicum, B. inopinatum, B. lactis, B. magnum, B. merycicum, B. minimum, B. pseudocatenulatum, B. pseudolongum, B. pullorum, B. ruminantium, B. saeculare, B. subtile, B. thermacidophilum B. thermophilum and B. tsurumiense.

According to a further preferred aspect of the invention, the bacteria of the Bacillus genus belong to at least one of the following species: Bacillus clausii, Bacillus subtilis, Bacillus coagulans, Bacillus megaterium Bacillus halodurans, Bacillus thuringiensis, Bacillus insolitus and Bacillus marinus.

According to a further preferred aspect of the invention, the bacteria of the Propionibacterium genus belong to at least one of the following species: P. shermanii, P. acnes, P. australiense, P. avidum, P. cyclohexanicum, P. freudenreichii, P. granulosum, P. jensenii, P. microaerophilum, P. propionicum and P. thoenii.

According to a further preferred aspect of the invention, the bacteria of the Streptococcus genus belong to at least one of the following species: Streptococcus thermophilus, Streptococcus salivarius, Streptococcus agalactiae, Streptococcus anginosus, Streptococcus bovis, Streptococcus canis, Streptococcus constellatus, Streptococcus downei, Streptococcus dysgalactiae, Streptococcus equinus, Streptococcus ferus, Streptococcus infantarius, Streptococcus iniae, Streptococcus intermedius, Streptococcus milleri, Streptococcus mitis, Streptococcus mutans, Streptococcus oralis, Streptococcus orisratti, Streptococcus parasanguinis, Streptococcus peroris, Streptococcus pneumoniae, Streptococcus pseudopneumoniae, Streptococcus pyogenes, Streptococcus ratti, Streptococcus tigurinus, Streptococcus sanguinis, Streptococcus sobrinus, Streptococcus suis, Streptococcus uberis, Streptococcus vestibularis, Streptococcus viridans and Streptococcus zooepidemicus.

According to a further preferred aspect of the invention, the bacteria of the Lactococcus genus belong to at least one of the following species: L. chungangensis, L. formosensis, L. fujiensis, L. garvieae, L. lactis, L. piscium, L. plantarum, L. raffinolactis and L. taiwanensis According to a further preferred aspect of the invention, the bacteria of the Aerococcus genus belong to at least one of the following species: A. urinae, A. sanguinicola, A. christensenii, A. suis, A. urinaeequi and A. urinaehominis.

According to a further preferred aspect of the invention, the bacteria of the Enterococcus genus belong to at least one of the following species: Enterococcus avium, Enterococcus durans, Enterococcus faecalis, Enterococcus faecium, Enterococcus gaffinarum, Enterococcus haemoperoxidus, Enterococcus hirae, Enterococcus malodoratus, Enterococcus moraviensis, Enterococcus mundtii, Enterococcus pseudoavium, Enterococcus raffinosus and Enterococcus solitarius.

According to a further preferred aspect of the invention, the yeasts belong preferably to the Saccharomyces genus, more preferably to the species Saccharomyces cerevisiae and/or Saccharomyces boulardii.

A further aspect of the present invention relates to a composition comprising the probiotics as described above.

The microorganisms of the composition of the present invention are preferably live, and thus the composition is also definable as probiotic. Alternatively, the microorganisms that can be used are dead or tyndallized.

In a further embodiment, the microorganisms are in the form of a lysate or extract and therefore the composition is also definable as a paraprobiotic, or a single component, or several components thereof, present at the level of the bacterial wall.

In a further embodiment of the invention, the composition further comprises the metabolic bioproducts generated by microorganisms, defined as postbiotics, and/or any other product of bacterial derivation. Therefore, the composition of the present invention is also a probiotic or a paraprobiotic or a postbiotic, known or presumed, or a component of the bacterial wall.

In general, the microorganisms comprised in the composition of the present invention are single microorganisms or combinations of any microbial species included in the QPS list of the EFSA.

Preferably the bacteria comprised in the composition are capable of surviving gastrointestinal transit and thus of reaching the colon live.

The microorganisms of the present invention are preferably administered in an amount ranging from 1 billion to 100 billion, more preferably 10-75 billion, even more preferably 15-50 billion, most preferably 20-30 billion cells, preferably bacterial cells, per administration.

According to a preferred aspect, the administration of microorganisms, preferably of bacteria, takes place at least 1-2 times a day.

Every route of administration is envisaged in the present invention. Preferably, the administration of the composition and/or probiotics, preferably based on bacteria, is oral, more preferably in the form of pills, capsules, tablets, granular powder, hard-shelled capsules, orally dissolving granules, sachets, lozenges or drinkable vials.

Alternatively, the composition of the invention and/or the probiotics, preferably based on bacteria, is (are) formulated as a liquid, for example as a syrup or beverage, or else it is (they are) added to food, for example to a yogurt, cheese or fruit juice. Alternatively, the composition of the invention and/or the probiotics, preferably based on bacteria, is (are) formulated in a form capable of exercising a topical action, for example as an enema.

The oral formulation of the composition and/or probiotics to which the present invention relates, preferably based on bacteria, further comprises excipients generally accepted for the production of probiotic and/or pharmaceutical products.

According to a preferred aspect of the invention, the composition further comprises anti-caking agents, preferably silicon dioxide or magnesium stearate.

According to a preferred aspect of the invention, the composition further comprises coating agents, preferably gelatine.

In a further embodiment of the invention, the composition of the invention comprises vitamins, trace elements, preferably zinc or selenium, enzymes and/or prebiotic substances, preferably fructo-oligosaccharides (FOS), galacto-oligosaccharides (GOS), inulin, guar gum or combinations thereof.

EXAMPLE

The experimental study underlying the present invention is based on biopsy samples isolated from 40 patients. The subjects were thus stratified:

10 patients with asymptomatic diverticulosis, 3 of whom female; age: 59-77);

10 patients with symptomatic uncomplicated diverticular disease (SUDD), 3 of whom female; age: 44-92);

10 patients with the symptomatic uncomplicated diverticular disease preceded by acute diverticulitis, 2 of whom female; age: 31-77);

10 patients without gastrointestinal problems, 6 of whom female; age: 33-75).

Six biopsy samples were obtained from the sigmoid colon of each patient; in the patients with diverticula, the biopsies were isolated in proximity thereto.

Informed consent was obtained from all patients and approval was obtained from the ethics committee of the University of Naples Federico II.

Figure 6:
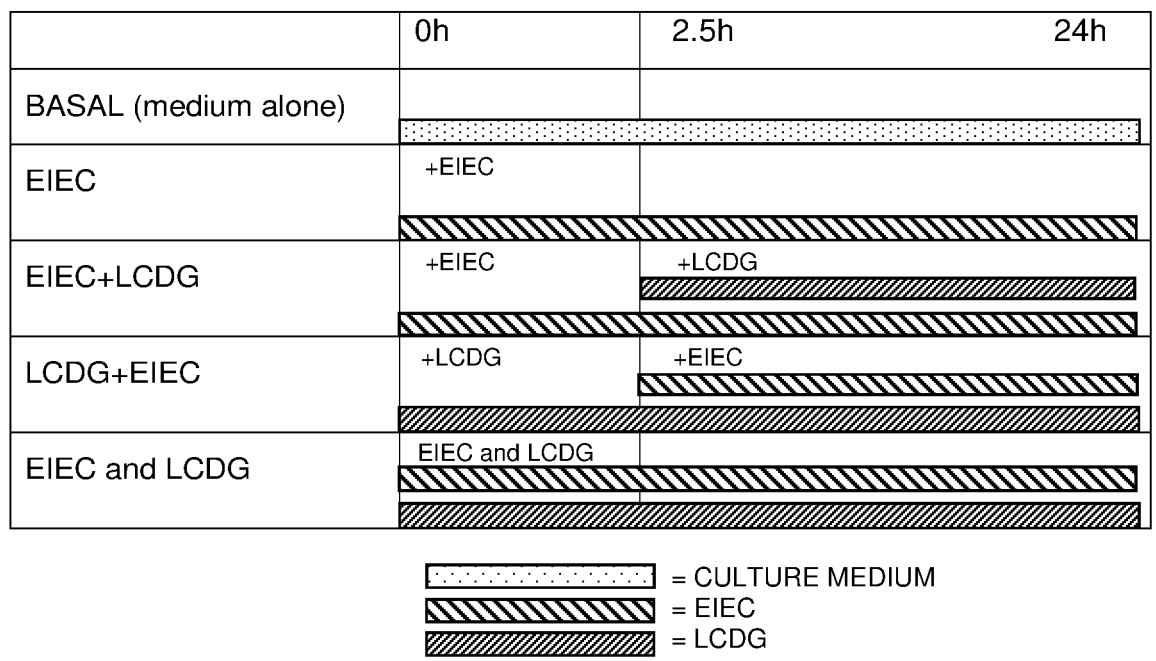
FIG. 6 is a table reporting results of experiments directed to the stimulation of biopsies with pathogenic and/or probiotic bacteria at the serosal side level as described in the Example.

The polarized biopsies were placed on a sterilized metal grid with the mucosal side down and the serosal side up. Then the metal grid was placed at the centre of an organ culture dish for 24 hours and maintained in DMEM-F12 at 37° C., in the presence of 95% oxygen and 5% CO2. The biopsies were then stimulated with the pathogenic and/or probiotic bacteria at the serosal side level as shown in FIG. 6.

The pathogenic bacteria used in the experiments were: Enteroinvasive *Escherichia coli* (EIEC); the probiotics tested were *Lactobacillus casei* DG® (*Lactobacillus paracasei* CNCM 11572; LCDG). The former was chosen for its harmful effects on the gastrointestinal tract, the latter for its probiotic effect.

The supernatants were subsequently recovered and the biopsies were treated with RIPA buffer. Both were frozen at −80° C.

Protein extraction was controlled by Western Blot as described in Turco, F. et al. 2015. The antibodies used were: rabbit anti-iNOS (1:500 vol/vol) or mouse anti-α actin (1:1000 vol/vol).

Nitric oxide (NO) was measured using the same technique already described in Turco, F. et al. 2015.

In the case of the ELISA test (Enzyme-Linked ImmunoSorbent Assay) that was used to measure S100B, the protocol followed was the one described in the manufacturer's manual.

The statistical analyses included analysis of variance and the Bonferroni multiple comparison test. The data presented are the mean±SD of the experiments. The level of statistical significance was fixed at $p<0.05$.

Basal Levels of iNOS Expression and Release of NO, S100B and Cytokines

The basal levels of expression and release of inflammation mediators in the gastrointestinal tract were measured.

Patients with diverticulosis showed a higher level of iNOS expression than healthy subjects (FIG. 1A).

Patients with symptomatic uncomplicated diverticular disease (SUDD) and symptomatic uncomplicated diverticular disease preceded by acute diverticulitis (SUDD+AD) showed greater differences in iNOS expression compared to healthy subjects (+2.04 and +2.86 times compared to the control—FIG. 1A).

Patients with asymptomatic diverticulosis and those with SUDD showed a slightly higher release of NO than healthy subjects (FIG. 1B). SUDD+AD patients showed a more marked difference (+7.77 times compared to the control—FIG. 1B).

The data shown in FIG. 10 indicate that there were no significant differences in the expression of the protein S100B (previously associated with the release of NO).

Figure 2:
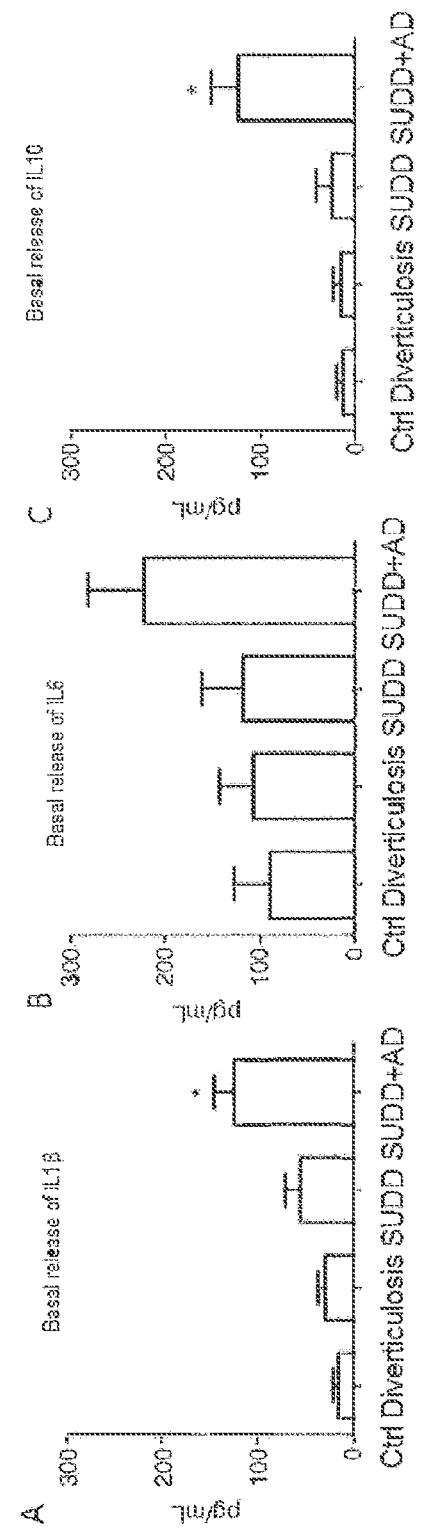
FIG. 2 shows the basal levels of the expression of A) IL-1β, B) IL-6 and C) IL-10 in the collected samples (Control, Diverticulosis, SUDD, SUDD+AD).

Furthermore, an increase in the release of the cytokine IL-1β was demonstrated, above all in the SUDD+AD patients compared to healthy subjects (FIG. 2A). The same pattern was also observed for the cytokine IL-6 (FIG. 2B). As for IL-10, an increase in the level of release was observed in particular in the SUDD+AD patients (FIG. 2C).

Effects of Bacterial Stimulation on iNOS Expression.

The effect on said values following bacterial stimulation on the expression of the inflammation mediator was subsequently tested both in healthy subjects and those with the various types of diverticulosis.

In particular, iNOS expression in mucosal biopsies was assessed.

Figure 3:
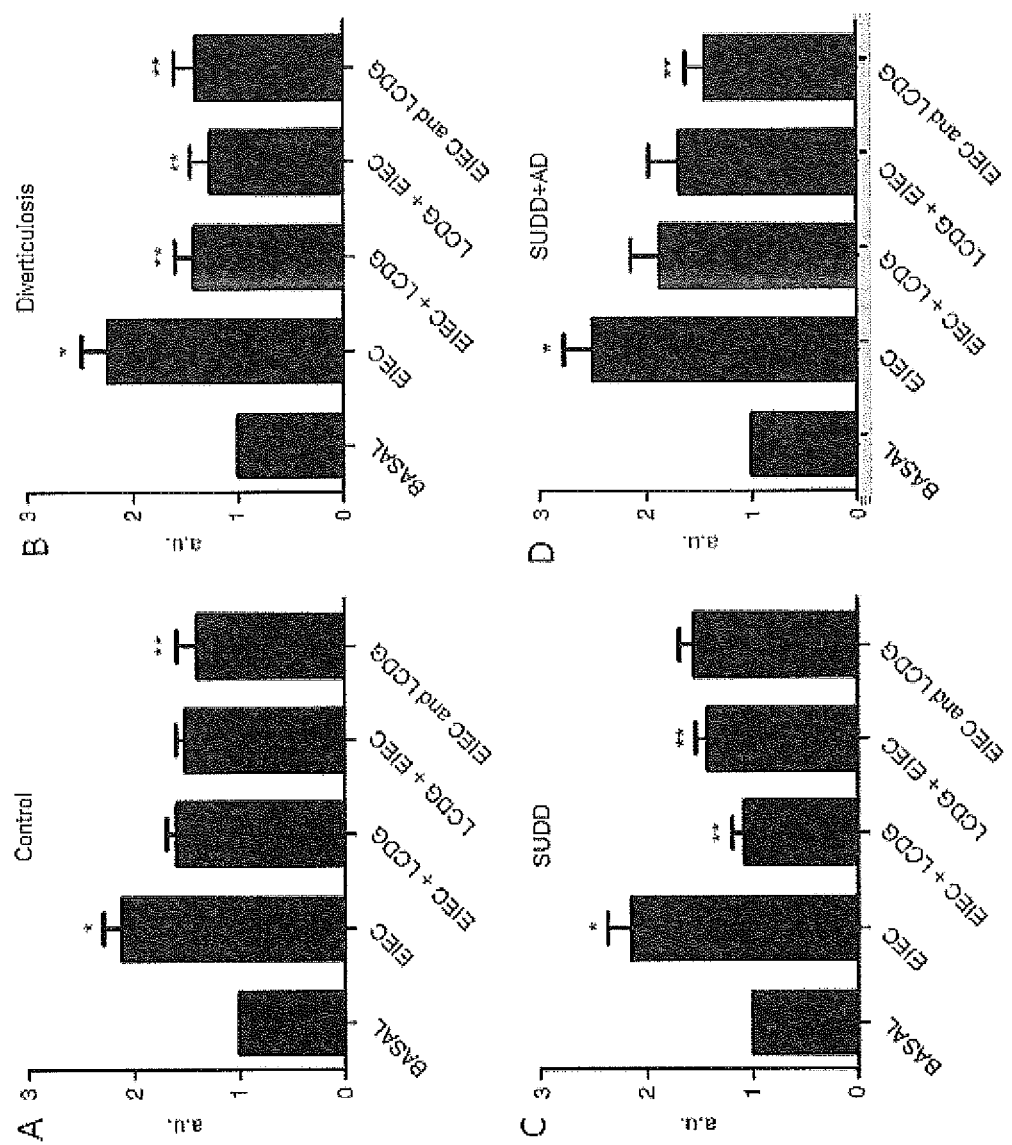
FIG. 3 shows the levels of iNOS expression before and after bacterial stimulation in the samples examined (A—Control, B—Diverticulosis, C—SUDD, D—SUDD+AD).

In healthy (control) subjects, the stimulation with EIEC brought about an increase in iNOS expression (+2.11 compared to basal—FIG. 3A). The addition of LCDG before or after EIEC did not alter iNOS expression, whereas when LCDG was added together with EIEC, a significant reduction in iNOS expression was observed (−1.50 times compared to stimulation with EIEC alone—FIG. 3A).

In the patients with diverticulosis as well, the presence of EIEC increased iNOS expression (+2.86 times compared to basal—FIG. 3B). In this case the addition of LCDG brought about a reduction in the level of iNOS expression compared to stimulation with EIEC alone, irrespective of the moment in which the bacteria was added to EIEC (FIG. 3B).

In patients with SUDD and SUDD+AD, the stimulation with EIEC caused iNOS expression to increase (+2.14 compared to basal—FIG. 3C). In this case the action of LCDG was more effective if administered with EIEC (FIG. 3C). Stimulation with LCDG did not in any case bring about an increase in the level of iNOS expression.

Effects of Bacterial Stimulation on the Release of NO.

Figure 4:
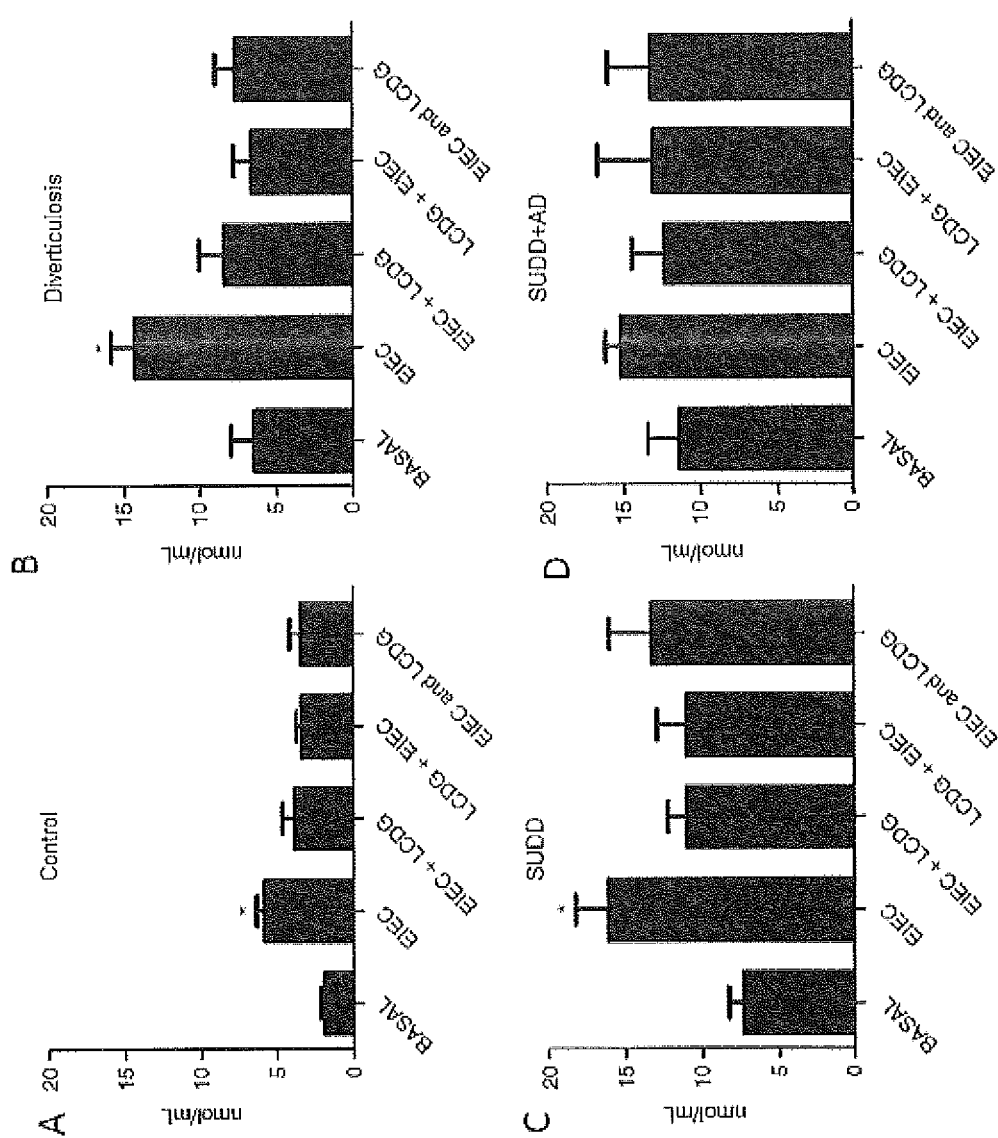
FIG. 4 shows the levels of NO released before and after bacterial stimulation in the samples examined (A—Control, B—Diverticulosis, C—SUDD, D—SUDD+AD).

In the samples of healthy subjects, the release of NO increased significantly following stimulation with EIEC (FIG. 4A). The addition of LCDG before, after, or together with EIEC significantly altered the basal value of NO.

The same effect was observed in the patients with asymptomatic diverticulosis and SUDD. In fact, the administration of EIEC increased the release of NO and the presence of LCDG cancelled out this effect (FIGS. 4B and 4C) irrespective of when LCDG was added.

The SUDD+AD patients showed a very high basal level of release of NO and thus the introduction of EIEC did not bring about a significant increase in these subjects. The addition of LCDG likewise did not bring about any change in the levels of release of NO due to the very high basal level (FIG. 4D).

Figure 5:
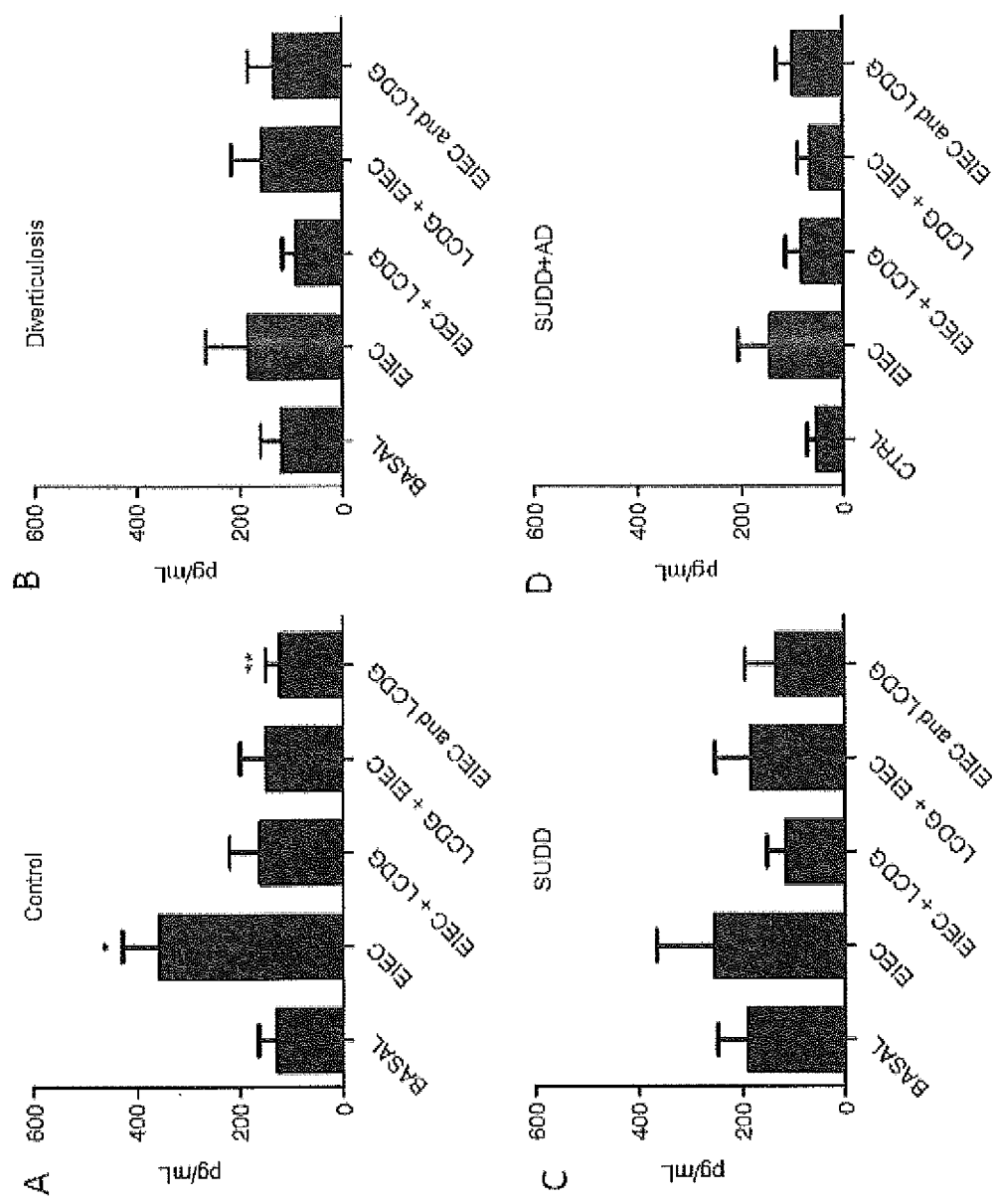
FIG. 5 shows the levels of release of the protein S100B before and after bacterial stimulation in the samples examined (A—Control, B—Diverticulosis, C—SUDD, D—SUDD+AD).

In the controls, stimulation with EIEC provoked an increase in the release of S100B (about +2.7 times compared to basal, p<0.05—FIG. 5A). Simultaneous stimulation with LCDG and EIEC provoked a reduction in the increase of S100B following the administration of EIEC (−2.90 times compared to EIEC, p<0.05—FIG. 5A).

The results set forth above demonstrate that the activation of the inflammation system dependent on NO (and correlated with iNOS expression) leads to a release of NO which increases progressively going from subjects with diverticulosis to SUDD+AD. INOS expression follows the same trend. In particular, in diverticulosis (increase of 1.5 versus the control), in SUDD (increase of 2 versus the control) and in SUDD+AD (increase of 3 versus the control). Furthermore, it was also demonstrated that the administration of LCDG prevents the observed effects. In particular, LCDG is capable of countering the effects of pathogenic bacteria, particularly in subjects with SUDD+AD.

These data clearly demonstrate that LCDG can be effectively used as a probiotic for the prevention and/or treatment, in subjects with diverticulosis, in particular diverticular disease SUDD and SUDD+AD, and/or symptoms associated therewith.

The invention claimed is:

1. A method for treating and/or preventing and/or reducing symptoms associated with diverticulosis or diverticular diseases, the method comprising
administering to a patient in need thereof a probiotic composition comprising *Lactobacillus paracasei* DG in combination with bacteria, yeast, and/or further microorganisms, wherein said bacteria belong to at least one genus each genus selected from *Lactobacillus, Bifidobacterium, Bacillus, Propionibacterium, Streptococcus, Lactococcus, Aerococcus, Enterococcus*, and combinations thereof
wherein the at least one genus is *Bifidobacterium*, and the bacteria belong to at least one of the following species: *B. animalis, B. bifidum, B. breve, B. infantis, B. longum, B. adolescentis, B. catenulatum, B. anqulatum, B. asteroides, B. bourn, B. choerinum, B. coryneforme, B. cuniculi, B. denticolens, B. dentium, B. gallicum, B. gallinarum, B. indicum, B. inopinatum, B. lactis, B. magnum, B. merycicum, B. minimum, B. pseudocatenulatum, B. pseudolongum, B. pullorum, B. ruminantium, B. saeculare, B. subtile, B. thermacidophilum, B. thermophilum* and *B. tsurumiense*.

2. The method according to claim 1, wherein the diverticular disease is symptomatic or asymptomatic.

3. The method according to claim 2, wherein the diverticular disease is Symptomatic Uncomplicated Diverticular Disease (SUDD), or Segmental Colitis Associated with Diverticolosis (SCAD).

4. The method according to claim 1, wherein the diverticulosis is associated with an overexpression of NO and/or iNOS and/or at least one pro-inflammatory cytokine.

5. The method according to claim 4, wherein the pro-inflammatory cytokine is selected from the group consisting of TNFα, IL1β, IL-6b, IL-10, and combinations thereof.

6. A method for treating and/or preventing and/or reducing symptoms associated with diverticulosis or diverticular diseases, the method comprising
administering to a patient in need thereof a probiotic composition comprising *Lactobacillus paracasei* DG in combination with bacteria, yeast, and/or further microorganisms, wherein said bacteria belong to at least one genus each genus selected from *Lactobacillus, Bifidobacterium, Bacillus, Propionibacterium, Streptococcus, Lactococcus, Aerococcus, Enterococcus*, and combinations thereof
wherein
the at least one genus is *Bacillus* genus, and the bacteria belong to at least one of the following species: *Bacillus clausii, Bacillus subtilis, Bacillus coagulans, Bacillus megaterium, Bacillus halodurans, Bacillus thuringiensis, Bacillus insolitus* and *Bacillus marinus*; and/or
the at least one genus is *Propionibacterium* genus, and the bacteria belong to at least one of the following species: *P. shermanii, P. acnes, P. australiense, P. avidum, P. cyclohexanicum, P. freudenreichii, P. granulosum, P. jensenii, P. microaerophilum, P. propionicum* and *P. thoenii*; and/or
the at least one genus is *Streptococcus* genus, and the bacteria belong to at least one of the following species: *Streptococcus thermophilus, Streptococcus salivarius, Streptococcus agalactiae, Streptococcus anginosus, Streptococcus bovis, Streptococcus canis, Streptococcus constellatus, Streptococcus downei, Streptococcus dysgalactiae, Streptococcus equinus, Streptococcus ferus, Streptococcus infantarius, Streptococcus iniae, Streptococcus intermedius, Streptococcus milleri,*

*Streptococcus mitis, Streptococcus mutans, Streptococcus oralis, Streptococcus orisratti, Streptococcus parasanguinis, Streptococcus peroris, Streptococcus pneumoniae, Streptococcus pseudopneumoniae, Streptococcus pyogenes, Streptococcus ratti, Streptococcus tigurinus, Streptococcus sanguinis, Streptococcus sobrinus, Streptococcus suis, Streptococcus uberis, Streptococcus vestibularis, Streptococcus viridans* and *Streptococcus zooepidemicus*; and/or the at least one genus is *Lactococcus* genus, and the bacteria belong to at least one of the following species: *L. chungangensis, L. formosensis, L. fujiensis, L. garvieae, L. lactis, L. piscium, L. plantarum, L. raffinolactis,* and *L. taiwanensis*; and/or the at least one genus is *Aerococcus* genus, and the bacteria belong to at least one of the following species: *A. urinae, A. sanguinicola, A. christensenii, A. suis, A. urinaeequi* and *A. urinaehominis*; and/or the at least one genus is *Enterococcus* genus, and the bacteria belong to at least one of the following species: *Enterococcus avium, Enterococcus durans, Enterococcus faecalis, Enterococcus faecium, Enterococcus gallinarum, Enterococcus haemoperoxidus, Enterococcus hirae, Enterococcus malodoratus, Enterococcus moraviensis, Enterococcus mundtii, Enterococcus pseudoavium, Enterococcus raffinosus* and *Enterococcus solitarius*.

7. A method for treating and/or preventing and/or reducing symptoms associated with diverticulosis or diverticular diseases, the method comprising administering to a patient in need thereof a probiotic composition comprising *Lactobacillus paracasei* DG in combination with bacteria, yeast, and/or further microorganisms, wherein said bacteria belong to at least one genus each genus selected from *Lactobacillus, Bifidobacterium, Bacillus, Propionibacterium, Streptococcus, Lactococcus, Aerococcus, Enterococcus*, and combinations thereof, wherein the yeasts belong to the *Saccharomyces* genus.

8. The method according to claim 7, wherein the yeasts belong to the species *Saccharomyces cerevisiae* and/or *Saccharomyces boulardii*.

9. The method according to claim 1, wherein the microorganisms are living and/or dead and/or tyndallized and/or as lysates and/or extracts.

10. The method according to claim 1, wherein the probiotic composition further comprises postbiotic metabolic products produced by the microorganisms and/or any further products deriving from the microorganisms.

11. The method according to claim 1, wherein the microorganisms and/or bacteria are administered in an amount ranging from 1 billion to 100 billion cells per dose, wherein the dose is administered 1-2 times daily.

12. The method of claim 11, wherein microorganisms and/or bacteria are administered in an amount ranging from 10-75 billion cells per dose.

13. The method of claim 12, wherein microorganisms and/or bacteria are administered in an amount ranging from 20-30 billion cells per dose.

14. The method according to claim 11, wherein said dose is for oral administration, as pills, capsules, tablets, granular powder, hard-shelled capsules, orally dissolving granules, sachets, lozenges or drinkable vials.

15. The method according to claim 1, wherein the probiotic composition is formulated as a syrup or a beverage; or added to food; or formulated to be administered topically as an enema.

16. The method according to claim 6, wherein the diverticular disease is symptomatic or asymptomatic.

17. The method according to claim 16, wherein the diverticular disease is Symptomatic Uncomplicated Diverticular Disease (SUDD), or Segmental Colitis Associated with Diverticolosis (SCAD).

18. The method according to claim 6, wherein the diverticulosis is associated with an overexpression of NO and/or iNOS and/or at least one pro-inflammatory cytokine.

19. The method according to claim 7, wherein the diverticular disease is symptomatic or asymptomatic.

20. The method according to claim 7, wherein the diverticulosis is associated with an overexpression of NO and/or iNOS and/or at least one pro-inflammatory cytokine.

\* \* \* \* \*